United States Patent
Medico et al.

(10) Patent No.: US 6,730,657 B1
(45) Date of Patent: May 4, 2004

(54) RECOMBINANT PROTEINS FROM HGF AND MSP

(75) Inventors: Enzo Medico, L'Aquila (IT); Paolo Michieli, L'Aquila (IT); Chiara Colessi, L'Aquila (IT); Gianfranco Caselli, L'Aquila (IT); Paolo Comoglio, L'Aquila (IT)

(73) Assignee: Dompe' S.p.A., L'Aquila (IT)

( * ) Notice: Subject to any disclaimer, the term of this patent is extended or adjusted under 35 U.S.C. 154(b) by 0 days.

(21) Appl. No.: 09/601,040

(22) PCT Filed: Jan. 28, 2000

(86) PCT No.: PCT/EP99/00502

§ 371 (c)(1),
(2), (4) Date: Sep. 8, 2000

(87) PCT Pub. No.: WO99/38968

PCT Pub. Date: Aug. 5, 1999

(30) Foreign Application Priority Data

Jan. 30, 1998 (IT) .......................................... MI98A0180

(51) Int. Cl.⁷ ...................... A61K 38/00; C07K 19/00; C07K 14/00; C07K 7/08; C07K 7/06
(52) U.S. Cl. ........................... 514/2; 530/402; 530/350; 530/300
(58) Field of Search .................. 424/130.1; 530/402, 530/350, 300; 435/69.1, 35, 7.1; 514/2

(56) References Cited

U.S. PATENT DOCUMENTS 5,350,836 A * 9/1994 Kopchick et al.

FOREIGN PATENT DOCUMENTS

| WO | 9323541 A1 | 11/1993 |
| WO | 9323550 A2 | 11/1993 |
| WO | 9406456 A1 | 3/1994 |

OTHER PUBLICATIONS

Michielli, et al, 2002, Nature Biotech., 20: 488–495.*
Waltz, et al, J. Biol. Chem., (1998), 272(48): 30526–30537; See Fig. 1.*
Danilkovich, A., et al (1999), J. Biol. Chem., 274(42): 29937–29943; esp. Fig. 4.*
Skolnick, J. (2000), Trends Biotech., 18(1):34–39, esp. p. 36.*
Smith et al. (1997), Nature Biotechnology 15:1222–1223.*
Pilbeam et al., 1993, Bone 14:717–720.*
Waltz, et al, J. Biol. Chem., (1998), 272(48): 30526–30537; See Fig. 1.*
Gheradrdi et al., CIBA Foundation Symposium, vol. 212, pp. 24–45 (1997).
Matsumoto et al., Biochemical and Biophysical Research, vol. 181, No. 2, pp. 691–699 (1991).
Waltz et al., The Journal of Biological Chemistry, vol. 272, No. 48, pp. 30526–37 (1997).

* cited by examiner

Primary Examiner—Elizabeth Kemmerer
Assistant Examiner—Sandra Wegert
(74) Attorney, Agent, or Firm—Birch, Stewart, Kolasch & Birch, LLP

(57) ABSTRACT

Recombinant proteins derived by recombination of structural domains obtained from alpha and beta subunits of HGF and/or MSP growth factors. These recombinant proteins contain domains selected from HGF and MSP, and are useful to protect cells, including differentiated cell elements of liver, kidney, and mucosa of the gastorenteral tract, from death (i.e., apoptosis) induced by chemotherapeutics.

6 Claims, 22 Drawing Sheets

FIGURE 1a

Figure 2A:
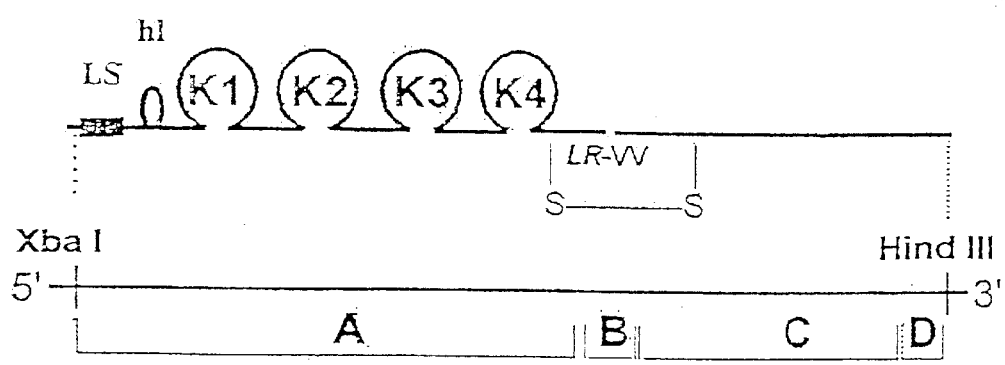

```
      ATGTGGGTGACCAAACTCCTGCCAGCCCTGCTGCTGCAGCATGTCCTCCTGCATCTCCTC
  1   ------------------------------------------------------------   60
      TACACCCACTGGTTTGAGGACGGTCGGGACGACGACGTCGTACAGGAGGACGTAGAGGAG

1   M  W  V  T  K  L  L  P  A  L  L  L  Q  H  V  L  L  H  L  L    20

CTGCTCCCCATCGCCATCCCCTATGCAGAGGGACAAAGGAAAAGAAGAAATACAATTCAT
 61   ------------------------------------------------------------  120
      GACGAGGGGTAGCGGTAGGGGATACGTCTCCCTGTTTCCTTTTCTTCTTTATGTTAAGTA

21   L  L  P  I  A  I  P  Y  A  E  G  Q  R  K  R  R  N  T  I  H    40

GAATTCAAAAAATCAGCAAAGACTACCCTAATCAAAATAGATCCAGCACTGAAGATAAAA
121   ------------------------------------------------------------  180
      CTTAAGTTTTTTAGTCGTTTCTGATGGGATTAGTTTTATCTAGGTCGTGACTTCTATTTT

41   E  F  K  K  S  A  K  T  T  L  I  K  I  D  P  A  L  K  I  K    60

ACCAAAAAAGTGAATACTGCAGACCAATGTGCTAATAGATGTACTAGGAATAAAGGACTT
181   ------------------------------------------------------------  240
      TGGTTTTTTCACTTATGACGTCTGGTTACACGATTATCTACATGATCCTTATTTCCTGAA

61   T  K  K  V  N  T  A  D  Q  C  A  N  R  C  T  R  N  K  G  L    80

CCATTCACTTGCAAGGCTTTTGTTTTTGATAAAGCAAGAAAACAATGCCTCTGGTTCCCC
241   ------------------------------------------------------------  300
      GGTAAGTGAACGTTCCGAAAACAAAAACTATTTCGTTCTTTTGTTACGGAGACCAAGGGG

81   P  F  T  C  K  A  F  V  F  D  K  A  R  K  Q  C  L  W  F  P   100

TTCAATAGCATGTCAAGTGGAGTGAAAAAAGAATTTGGCCATGAATTTGACCTCTATGAA
301   ------------------------------------------------------------  360
      AAGTTATCGTACAGTTCACCTCACTTTTTTCTTAAACCGGTACTTAAACTGGAGATACTT

101   F  N  S  M  S  S  G  V  K  K  E  F  G  H  E  F  D  L  Y  E   120

AACAAAGACTACATTAGAAACTGCATCATTGGTAAAGGACGCAGCTACAAGGGAACAGTA
361   ------------------------------------------------------------  420
      TTGTTTCTGATGTAATCTTTGACGTAGTAACCATTTCCTGCGTCGATGTTCCCTTGTCAT

121   N  K  D  Y  I  R  N  C  I  I  G  K  G  R  S  Y  K  G  T  V   140

TCTATCACTAAGAGTGGCATCAAATGTCAGCCCTGGAGTTCCATGATACCACACGAACAC
421   ------------------------------------------------------------  480
      AGATAGTGATTCTCACCGTAGTTTACAGTCGGGACCTCAAGGTACTATGGTGTGCTTGTG

141   S  I  T  K  S  G  I  K  C  Q  P  W  S  S  M  I  P  H  E  H   160

AGCTATCGGGGTAAAGACCTACAGGAAAACTACTGTCGAAATCCTCGAGGGGAAGAAGGG
481   ------------------------------------------------------------  540
      TCGATAGCCCCATTTCTGGATGTCCTTTTGATGACAGCTTTAGGAGCTCCCCTTCTTCCC

161   S  Y  R  G  K  D  L  Q  E  N  Y  C  R  N  P  R  G  E  E  G   180

GGACCCTGGTGTTTCACAAGCAATCCAGAGGTACGCTACGAAGTCTGTGACATTCCTCAG
541   ------------------------------------------------------------  600
      CCTGGGACCACAAAGTGTTCGTTAGGTCTCCATGCGATGCTTCAGACACTGTAAGGAGTC

181   G  P  W  C  F  T  S  N  P  E  V  R  Y  E  V  C  D  I  P  Q   200
```

(continued)

(continued)

```
      TGTTCAGAAGTTGAATGCATGACCTGCAATGGGGAGAGTTATCGAGGTCTCATGGATCAT
601   ------------------------------------------------------------ 660
      ACAAGTCTTCAACTTACGTACTGGACGTTACCCCTCTCAATAGCTCCAGAGTACCTAGTA

201    C  S  E  V  E  C  M  T  C  N  G  E  S  Y  R  G  L  M  D  H    220

ACAGAATCAGGCAAGATTTGTCAGCGCTGGGATCATCAGACACCACACCGGCACAAATTC
661   ------------------------------------------------------------ 720
      TGTCTTAGTCCGTTCTAAACAGTCGCGACCCTAGTAGTCTGTGGTGTGGCCGTGTTTAAG

221    T  E  S  G  K  I  C  Q  R  W  D  H  Q  T  P  H  R  H  K  F    240

TTGCCTGAAAGATATCCCGACAAGGGCTTTGATGATAATTATTGCCGCAATCCCGATGGC
721   ------------------------------------------------------------ 780
      AACGGACTTTCTATAGGGCTGTTCCCGAAACTACTATTAATAACGGCGTTAGGGCTACCG

241    L  P  E  R  Y  P  D  K  G  F  D  D  N  Y  C  R  N  P  D  G    260

CAGCCGAGGCCATGGTGCTATACTCTTGACCCTCACACCCGCTGGGAGTACTGTGCAATT
781   ------------------------------------------------------------ 840
      GTCGGCTCCGGTACCACGATATGAGAACTGGGAGTGTGGGCGACCCTCATGACACGTTAA

261    Q  P  R  P  W  C  Y  T  L  D  P  H  T  R  W  E  Y  C  A  I    280

AAAACATGCGCTGACAATACTATGAATGACACTGATGTTCCTTTGGAAACAACTGAATGC
841   ------------------------------------------------------------ 900
      TTTTGTACGCGACTGTTATGATACTTACTGTGACTACAAGGAAACCTTTGTTGACTTACG

281    K  T  C  A  D  N  T  M  N  D  T  D  V  P  L  E  T  T  E  C    300

ATCCAAGGTCAAGGAGAAGGCTACAGGGGCACTGTCAATACCATTTGGAATGGAATTCCA
901   ------------------------------------------------------------ 960
      TAGGTTCCAGTTCCTCTTCCGATGTCCCCGTGACAGTTATGGTAAACCTTACCTTAAGGT

301    I  Q  G  Q  G  E  G  Y  R  G  T  V  N  T  I  W  N  G  I  P    320

TGTCAGCGTTGGGATTCTCAGTATCCTCACGAGCATGACATGACTCCTGAAAATTTCAAG
961   ------------------------------------------------------------ 1020
      ACAGTCGCAACCCTAAGAGTCATAGGAGTGCTCGTACTGTACTGAGGACTTTTAAAGTTC

321    C  Q  R  W  D  S  Q  Y  P  H  E  H  D  M  T  P  E  N  F  K    340

TGCAAGGACCTACGAGAAAATTACTGCCGAAATCCAGATGGGTCTGAATCACCCTGGTGT
1021  ------------------------------------------------------------ 1080
      ACGTTCCTGGATGCTCTTTTAATGACGGCTTTAGGTCTACCCAGACTTAGTGGGACCACA

341    C  K  D  L  R  E  N  Y  C  R  N  P  D  G  S  E  S  P  W  C    360

TTTACCACTGATCCAAACATCCGAGTTGGCTACTGCTCCCAAATTCCAAACTGTGATATG
1081  ------------------------------------------------------------ 1140
      AAATGGTGACTAGGTTTGTAGGCTCAACCGATGACGAGGGTTTAAGGTTTGACACTATAC

361    F  T  T  D  P  N  I  R  V  G  Y  C  S  Q  I  P  N  C  D  M    380

TCACATGGACAAGATTGTTATCGTGGGAATGGCAAAAATTATATGGGCAACTTATCCCAA
1141  ------------------------------------------------------------ 1200
      AGTGTACCTGTTCTAACAATAGCACCCTTACCGTTTTTAATATACCCGTTGAATAGGGTT

381    S  H  G  Q  D  C  Y  R  G  N  G  K  N  Y  M  G  N  L  S  Q    400

ACAAGATCTGGACTAACATGTTCAATGTGGGACAAGAACATGGAAGACTTACATCGTCAT
1201  ------------------------------------------------------------ 1260
      TGTTCTAGACCTGATTGTACAAGTTACACCCTGTTCTTGTACCTTCTGAATGTAGCAGTA

401    T  R  S  G  L  T  C  S  M  W  D  K  N  M  E  D  L  H  R  H    420
```

(continued)

(continued)

```
      ATCTTCTGGGAACCAGATGCAAGTAAGCTGAATGAGAATTACTGCCGAAATCCAGATGAT
1261  ------------------------------------------------------------  1320
      TAGAAGACCCTTGGTCTACGTTCATTCGACTTACTCTTAATGACGGCTTTAGGTCTACTA

421   I  F  W  E  P  D  A  S  K  L  N  E  N  Y  C  R  N  P  D  D   440

GACGCTCATGGACCCTGGTGCTACACGGGAAATCCACTCATTCCTTGGGATTATTGCCCT
1321  ------------------------------------------------------------  1380
      CTGCGAGTACCTGGGACCACGATGTGCCCTTTAGGTGAGTAAGGAACCCTAATAACGGGA

441   D  A  H  G  P  W  C  Y  T  G  N  P  L  I  P  W  D  Y  C  P   460

ATTTCTCGTTGTGAAGGTGATACCACACCTACAATAGTCAATTTAGACCATCCCGTAATA
1381  ------------------------------------------------------------  1440
      TAAAGAGCAACACTTCCACTATGGTGTGGATGTTATCAGTTAAATCTGGTAGGGCATTAT

461   I  S  R  C  E  G  D  T  T  P  T  I  V  N  L  D  H  P  V  I   480

TCTTGTGCCAAAACGAAACAATTGCGAGTTGTAAATGGGATTCCAACACGAACAAACATA
1441  ------------------------------------------------------------  1500
      AGAACACGGTTTTGCTTTGTTAACGCTCAACATTTACCCTAAGGTTGTGCTTGTTTGTAT

481   S  C  A  K  T  K  Q  L  R  V  V  N  G  I  P  T  R  T  N  I   500

GGATGGATGGTTAGTTTGAGATACAGAAATAAACATATCTGCGGAGGATCATTGATAAAG
1501  ------------------------------------------------------------  1560
      CCTACCTACCAATCAAACTCTATGTCTTTATTTGTATAGACGCCTCCTAGTAACTATTTC

501   G  W  M  V  S  L  R  Y  R  N  K  H  I  C  G  G  S  L  I  K   520

GAGAGTTGGGTTCTTACTGCACGACAGTGTTTCCCTTCTCGAGACTTGAAAGATTATGAA
1561  ------------------------------------------------------------  1620
      CTCTCAACCCAAGAATGACGTGCTGTCACAAAGGGAAGAGCTCTGAACTTTCTAATACTT

521   E  S  W  V  L  T  A  R  Q  C  F  P  S  R  D  L  K  D  Y  E   540

GCTTGGCTTGGAATTCATGATGTCCACGGAAGAGGAGATGAGAAATGCAAACAGGTTCTC
1621  ------------------------------------------------------------  1680
      CGAACCGAACCTTAAGTACTACAGGTGCCTTCTCCTCTACTCTTTACGTTTGTCCAAGAG

541   A  W  L  G  I  H  D  V  H  G  R  G  D  E  K  C  K  Q  V  L   560

AATGTTTCCCAGCTGGTATATGGCCCTGAAGGATCAGATCTGGTTTTAATGAAGCTTGCC
1681  ------------------------------------------------------------  1740
      TTACAAAGGGTCGACCATATACCGGGACTTCCTAGTCTAGACCAAAATTACTTCGAACGG

561   N  V  S  Q  L  V  Y  G  P  E  G  S  D  L  V  L  M  K  L  A   580

AGGCCTGCTGTCCTGGATGATTTTGTTAGTACGATTGATTTACCTAATTATGGATGCACA
1741  ------------------------------------------------------------  1800
      TCCGGACGACAGGACCTACTAAAACAATCATGCTAACTAAATGGATTAATACCTACGTGT

581   R  P  A  V  L  D  D  F  V  S  T  I  D  L  P  N  Y  G  C  T   600
```

(continued)

(continued)

```
      ATTCCTGAAAAGACCAGTTGCAGTGTTTATGGCTGGGGCTACACTGGATTGATCAACTAT
1801  ------------+---------+---------+---------+---------+---------+  1860
      TAAGGACTTTTCTGGTCAACGTCACAAATACCGACCCCGATGTGACCTAACTAGTTGATA

601    I  P  E  K  T  S  C  S  V  Y  G  W  G  Y  T  G  L  I  N  Y    620

GATGGCCTATTACGAGTGGCACATCTCTATATAATGGGAAATGAGAAATGCAGCCAGCAT
1861  ---------+---------+---------+---------+---------+---------+  1920
      CTACCGGATAATGCTCACCGTGTAGAGATATATTACCCTTTACTCTTTACGTCGGTCGTA

621    D  G  L  L  R  V  A  H  L  Y  I  M  G  N  E  K  C  S  Q  H    640

CATCGAGGGAAGGTGACTCTGAATGAGTCTGAAATATGTGCTGGGGCTGAAAAGATTGGA
1921  ---------+---------+---------+---------+---------+---------+  1980
      GTAGCTCCCTTCCACTGAGACTTACTCAGACTTTATACACGACCCCGACTTTTCTAACCT

641    H  R  G  K  V  T  L  N  E  S  E  I  C  A  G  A  E  K  I  G    660

TCAGGACCATGTGAGGGGGATTATGGTGGCCCACTTGTTTGTGAGCAACATAAAATGAGA
1981  ---------+---------+---------+---------+---------+---------+  2040
      AGTCCTGGTACACTCCCCCTAATACCACCGGGTGAACAAACACTCGTTGTATTTTACTCT

661    S  G  P  C  E  G  D  Y  G  G  P  L  V  C  E  Q  H  K  M  R    680

ATGGTTCTTGGTGTCATTGTTCCTGGTCGTGGATGTGCCATTCCAAATCGTCCTGGTATT
2041  ---------+---------+---------+---------+---------+---------+  2100
      TACCAAGAACCACAGTAACAAGGACCAGCACCTACACGGTAAGGTTTAGCAGGACCATAA

681    M  V  L  G  V  I  V  P  G  R  G  C  A  I  P  N  R  P  G  I    700

TTTGTCCGAGTAGCATATTATGCAAAATGGATACACAAAATTATTTTAACATATAAGGTA
2101  ---------+---------+---------+---------+---------+---------+  2160
      AAACAGGCTCATCGTATAATACGTTTTACCTATGTGTTTTAATAAAATTGTATATTCCAT

701    F  V  R  V  A  Y  Y  A  K  W  I  H  K  I  I  L  T  Y  K  V    720

CCACAGTCATAG
2161  ---------+--  2172
      GGTGTCAGTATC

721    P  Q  S  *    723
```

FIGURE 1b

```
  1  ATGGGGTGGCTCCCACTCCTGCTGCTTCTGACTCAATGCTTAGGGGTCCCTGGGCAGCGC
     ------------+---------+---------+---------+---------+----------   60
     TACCCCACCGAGGGTGAGGACGACGAAGACTGAGTTACGAATCCCCAGGGACCCGTCGCG

1  M  G  W  L  P  L  L  L  L  T  Q  C  L  G  V  P  G  Q  R    20

61  TCGCCATTGAATGACTTCCAAGTGCTCCGGGGCACAGAGCTACAGCACCTGCTACATGCG
     ------------+---------+---------+---------+---------+----------  120
     AGCGGTAACTTACTGAAGGTTCACGAGGCCCCGTGTCTCGATGTCGTGGACGATGTACGC

21  S  P  L  N  D  F  Q  V  L  R  G  T  E  L  Q  H  L  L  H  A   40

121  GTGGTGCCCGGGCCTTGGCAGGAGGATGTGGCAGATGCTGAAGAGTGTGCTGGTCGCTGT
     ------------+---------+---------+---------+---------+----------  180
     CACCACGGGCCCGGAACCGTCCTCCTACACCGTCTACGACTTCTCACACGACCAGCGACA

41  V  V  P  G  P  W  Q  E  D  V  A  D  A  E  E  C  A  G  R  C   60

181  GGGCCCTTAATGGACTGCCGGGCCTTCCACTACAACGTGAGCAGCCATGGTTGCCAACTG
     ------------+---------+---------+---------+---------+----------  240
     CCCGGGAATTACCTGACGGCCCGGAAGGTGATGTTGCACTCGTCGGTACCAACGGTTGAC

61  G  P  L  M  D  C  R  A  F  H  Y  N  V  S  S  H  G  C  Q  L   80

241  CTGCCATGGACTCAACACTCGCCCCACACGAGGCTGCGGCGTTCTGGGCGCTGTGACCTC
     ------------+---------+---------+---------+---------+----------  300
     GACGGTACCTGAGTTGTGAGCGGGGTGTGCTCCGACGCCGCAAGACCCGCGACACTGGAG

81  L  P  W  T  Q  H  S  P  H  T  R  L  R  R  S  G  R  C  D  L  100

301  TTCCAGAAGAAAGACTACGTACGGACCTGCATCATGAACAATGGGGTTGGGTACCGGGGC
     ------------+---------+---------+---------+---------+----------  360
     AAGGTCTTCTTTCTGATGCATGCCTGGACGTAGTACTTGTTACCCCAACCCATGGCCCCG

101  F  Q  K  K  D  Y  V  R  T  C  I  M  N  N  G  V  G  Y  R  G  120

361  ACCATGGCCACGACCGTGGGTGGCCTGCCCTGCCAGGCTTGGAGCCACAAGTTCCCGAAT
     ------------+---------+---------+---------+---------+----------  420
     TGGTACCGGTGCTGGCACCCACCGGACGGGACGGTCCGAACCTCGGTGTTCAAGGGCTTA

121  T  M  A  T  T  V  G  G  L  P  C  Q  A  W  S  H  K  F  P  N  140

421  GATCACAAGTACACGCCCACTCTCCGGAATGGCCTGGAAGAGAACTTCTGCCGTAACCCT
     ------------+---------+---------+---------+---------+----------  480
     CTAGTGTTCATGTGCGGGTGAGAGGCCTTACCGGACCTTCTCTTGAAGACGGCATTGGGA

141  D  H  K  Y  T  P  T  L  R  N  G  L  E  E  N  F  C  R  N  P  160
```

(continued)

(continued)

```
      GATGGCGACCCCGGAGGTCCTTGGTGCTACACAACAGACCCTGCTGTGCGCTTCCAGAGC
481   ------------------------------------------------------------  540
      CTACCGCTGGGGCCTCCAGGAACCACGATGTGTTGTCTGGGACGACACGCGAAGGTCTCG

161   D  G  D  P  G  G  P  W  C  Y  T  T  D  P  A  V  R  F  Q  S    180

TGCGGCATCAAATCCTGCCGGGAGGCCGCGTGTGTCTGGTGCAATGGCGAGGAATACCGC
531   ------------------------------------------------------------  590
      ACGCCGTAGTTTAGGACGGCCCTCCGGCGCACACAGACCACGTTACCGCTCCTTATGGCG

181   C  G  I  K  S  C  R  E  A  A  C  V  W  C  N  G  E  E  Y  R    200

GGCGCGGTAGACCGCACGGAGTCAGGGCGCGAGTGCCAGCGCTGGGATCTTCAGCACCCG
601   ------------------------------------------------------------  660
      CCGCGCCATCTGGCGTGCCTCAGTCCCGCGCTCACGGTCGCGACCCTAGAAGTCGTGGGC

201   G  A  V  D  R  T  E  S  G  R  E  C  Q  R  W  D  L  Q  H  P    220

CACCAGCACCCCTTCGAGCCGGGCAAGTTCCTCGACCAAGGTCTGGACGACAACTATTGC
661   ------------------------------------------------------------  720
      GTGGTCGTGGGGAAGCTCGGCCCGTTCAAGGAGCTGGTTCCAGACCTGCTGTTGATAACG

221   H  Q  H  P  F  E  P  G  K  F  L  D  Q  G  L  D  D  N  Y  C    240

CGGAATCCTGACGGCTCCGAGCGGCCATGGTGCTACACTACGGATCCGCAGATCGAGCGA
721   ------------------------------------------------------------  780
      GCCTTAGGACTGCCGAGGCTCGCCGGTACCACGATGTGATGCCTAGGCGTCTAGCTCGCT

241   R  N  P  D  G  S  E  R  P  W  C  Y  T  T  D  P  Q  I  E  R    260

GAGTTCTGTGACCTCCCCCGCTGCGGGTCCGAGGCACAGCCCCGCCAAGAGGCCACAACT
781   ------------------------------------------------------------  840
      CTCAAGACACTGGAGGGGGCGACGCCCAGGCTCCGTGTCGGGGCGGTTCTCCGGTGTTGA

261   E  F  C  D  L  P  R  C  G  S  E  A  Q  P  R  Q  E  A  T  T    280

GTCAGCTGCTTCCGCGGGAAGGGTGAGGGCTACCGGGGCACAGCCAATACCACCACTGCG
841   ------------------------------------------------------------  900
      CAGTCGACGAAGGCGCCCTTCCCACTCCCGATGGCCCCGTGTCGGTTATGGTGGTGACGC

281   V  S  C  F  R  G  K  G  E  G  Y  R  G  T  A  N  T  T  T  A    300

GGCGTACCTTGCCAGCGTTGGGACGCGCAAATCCCGCATCAGCACCGATTTACGCCAGAA
901   ------------------------------------------------------------  960
      CCGCATGGAACGGTCGCAACCCTGCGCGTTTAGGGCGTAGTCGTGGCTAAATGCGGTCTT

301   G  V  P  C  Q  R  W  D  A  Q  I  P  H  Q  H  R  F  T  P  E    320

AAATACGCGTGCAAAGACCTTCGGGAGAACTTCTGCCGGAACCCCGACGGCTCAGAGGCG
961   ------------------------------------------------------------  1020
      TTTATGCGCACGTTTCTGGAAGCCCTCTTGAAGACGGCCTTGGGGCTGCCGAGTCTCCGC

321   K  Y  A  C  K  D  L  R  E  N  F  C  R  N  P  D  G  S  E  A    340

CCCTGGTGCTTCACACTGCGGCCCGGCATGCGCGCGGCCTTTTGCTACCAGATCCGGCGT
1021  ------------------------------------------------------------  1080
      GGGACCACGAAGTGTGACGCCGGGCCGTACGCGCGCCGGAAAACGATGGTCTAGGCCGCA

341   P  W  C  F  T  L  R  P  G  M  R  A  A  F  C  Y  Q  I  R  R    360

TGTACAGACGACGTGCGGCCCCAGGACTGCTACCACGGCGCAGGGGAGCAGTACCGCGGC
1081  ------------------------------------------------------------  1140
      ACATGTCTGCTGCACGCCGGGGTCCTGACGATGGTGCCGCGTCCCCTCGTCATGGCGCCG

361   C  T  D  D  V  R  P  Q  D  C  Y  H  G  A  G  E  Q  Y  R  G    380
```

(continued)

(continued)

```
1141 ACGGTCAGCAAGACCCGCAAGGGTGTCCAGTGCCAGCGCTGGTCCGCTGAGACGCCGCAC 1200
     TGCCAGTCGTTCTGGGCGTTCCCACAGGTCACGGTCGCGACCAGGCGACTCTGCGGCGTG
 381 T  V  S  K  T  R  K  G  V  Q  C  Q  R  W  S  A  E  T  P  H    400

1201 AAGCCGCAGTTCACGTTTACCTCCGAACCGCATGCACAACTGGAGGAGAACTTCTGCCGG 1260
     TTCGGCGTCAAGTGCAAATGGAGGCTTGGCGTACGTGTTGACCTCCTCTTGAAGACGGCC
 401 K  P  Q  F  T  F  T  S  E  P  H  A  Q  L  E  E  N  F  C  R    420

1261 AACCCAGATGGGGATAGCCATGGGCCCTGGTGCTACACGATGGACCCAAGGACCCCATTC 1320
     TTGGGTCTACCCCTATCGGTACCCGGGACCACGATGTGCTACCTGGGTTCCTGGGGTAAG
 421 N  P  D  G  D  S  H  G  P  W  C  Y  T  M  D  P  R  T  P  F    440

1321 GACTACTGTGCCCTGCGACGCTGCGCTGATGACCAGCCGCCATCAATCCTGGACCCCCCA 1380
     CTGATGACACGGGACGCTGCGACGCGACTACTGGTCGGCGGTAGTTAGGACCTGGGGGGT
 441 D  Y  C  A  L  R  R  C  A  D  D  Q  P  P  S  I  L  D  P  P    460

1381 GACCAGGTGCAGTTTGAGAAGTGTGGCAAGAGGGTGGATCGGCTGGATCAGCGGCGTTCC 1440
     CTGGTCCACGTCAAACTCTTCACACCGTTCTCCCACCTAGCCGACCTAGTCGCCGCAAGG
 461 D  Q  V  Q  F  E  K  C  G  K  R  V  D  R  L  D  Q  R  R  S    480

1441 AAGCTGCGCGTGGTTGGGGGCCATCCGGGCAACTCACCCTGGACAGTCAGCTTGCGGAAT 1500
     TTCGACGCGCACCAACCCCCGGTAGGCCCGTTGAGTGGGACCTGTCAGTCGAACGCCTTA
 481 K  L  R  V  V  G  G  H  P  G  N  S  P  W  T  V  S  L  R  N    500

1501 CGGCAGGGCCAGCATTTCTGCGGGGGTCTCTAGTGAAGGAGCAGTGGATACTGACTGCC 1560
     GCCGTCCCGGTCGTAAAGACGCCCCCAGAGATCACTTCCTCGTCACCTATGACTGACGG
 501 R  Q  G  Q  H  F  C  G  G  S  L  V  K  E  Q  W  I  L  T  A    520

1561 CGGCAGTGCTTCTCCTCCTGCCATATGCCTCTCACGGGCTATGAGGTATGGTTGGGCACC 1620
     GCCGTCACGAAGAGGAGGACGGTATACGGAGAGTGCCCGATACTCCATACCAACCCGTGG
 521 R  Q  C  F  S  S  C  H  M  P  L  T  G  Y  E  V  W  L  G  T    540

1621 CTGTTCCAGAACCCACAGCATGGAGAGCCAAGCCTACAGCGGGTCCCAGTAGCCAAGATG 1680
     GACAAGGTCTTGGGTGTCGTACCTCTCGGTTCGGATGTCGCCCAGGGTCATCGGTTCTAC
 541 L  F  Q  N  P  Q  H  G  E  P  S  L  Q  R  V  P  V  A  K  M    560

1681 GTGTGTGGCCCTCAGGCTCCCAGCTTGTCCTGCTCAAGCTGGAGAGATCTGTGACCCTG 1740
     CACACACCCGGGAGTCCGAGGGTCGAACAGGACGAGTTCGACCTCTCTAGACACTGGGAC
 561 V  C  G  P  S  G  S  Q  L  V  L  L  K  L  E  R  S  V  T  L    580

1741 AACCAGCGTGTGGCCCTGATCTGCCTGCCCCCTGAATGGTATGTGGTGCCTCCAGGGACC 1800
     TTGGTCGCACACCGGGACTAGACGGACGGGGACTTACCATACACCACGGAGGTCCCTGG
 581 N  Q  R  V  A  L  I  C  L  P  P  E  W  Y  V  V  P  P  G  T    600
```

(continued)

(continued)

```
1801  AAGTGTGAGATTGCAGGCTGGGGTGAGACCAAAGGTACGGGTAATGACACAGTCCTAAAT
      ------------+---------+---------+---------+---------+---------  1860
      TTCACACTCTAACGTCCGACCCCACTCTGGTTTCCATGCCCATTACTGTGTCAGGATTTA

601    K  C  E  I  A  G  W  G  E  T  K  G  T  G  N  D  T  V  L  N    620

1861  GTGGCCTTTCTGAATGTTATCTCCAACCAGGAGTGTAACATCAAGCACCGAGGACGTGTG
      ------------+---------+---------+---------+---------+---------  1920
      CACCGGAAAGACTTACAATAGAGGTTGGTCCTCACATTGTAGTTCGTGGCTCCTGCACAC

621    V  A  F  L  N  V  I  S  N  Q  E  C  N  I  K  H  R  G  R  V    640

1921  CGGGAGAGTGAGATGTGCACTGAGGGACTGTTGGCCCCTGTGGGGGCCTGTGAGGGTGAC
      ------------+---------+---------+---------+---------+---------  1980
      GCCCTCTCACTCTACACGTGACTCCCTGACAACCGGGGACACCCCCGGACACTCCCACTG

641    R  E  S  E  M  C  T  E  G  L  L  A  P  V  G  A  C  E  G  D    660

1981  TACGGGGGCCCACTTGCCTGCTTTACCCACAACTGCTGGGTCCTGGAAGGAATTATAATC
      ------------+---------+---------+---------+---------+---------  2040
      ATGCCCCCGGGTGAACGGACGAAATGGGTGTTGACGACCCAGGACCTTCCTTAATATTAG

661    Y  G  G  P  L  A  C  F  T  H  N  C  W  V  L  E  G  I  I  I    680

2041  CCCAACCGAGTATGCGCAAGGTCCCGCTGGCCAGCTGTCTTCACGCGTGTCTCTGTGTTT
      ------------+---------+---------+---------+---------+---------  2100
      GGGTTGGCTCATACGCGTTCCAGGGCGACCGGTCGACAGAAGTGCGCACAGAGACACAAA

681    P  N  R  V  C  A  R  S  R  W  P  A  V  F  T  R  V  S  V  F    700

2101  GTGGACTGGATTCACAAGGTCATGAGACTGGGTTAG
      ------------+---------+---------    2136
      CACCTGACCTAAGTGTTCCAGTACTCTGACCCAATC

701    V  D  W  I  E  K  V  M  R  L  G  *    711
```

FIGURE 2b

```
  1  ATGTGGGTGACCAAACTCCTGCCAGCCCTGCTGCTGCAGCATGTCCTCCTGCATCTCCTC
     ------------+---------+---------+---------+---------+---------+  60
     TACACCCACTGGTTTGAGGACGGTCGGGACGACGACGTCGTACAGGAGGACGTAGAGGAG

1  M  W  V  T  K  L  L  P  A  L  L  L  Q  H  V  L  L  H  L  L    20

61  CTGCTCCCCATCGCCATCCCCTATGCAGAGGGACAAAGGAAAAGAAGAAATACAATTCAT
     ------------+---------+---------+---------+---------+---------+ 120
     GACGAGGGGTAGCGGTAGGGGATACGTCTCCCTGTTTCCTTTTCTTCTTTATGTTAAGTA

21  L  L  P  I  A  I  P  Y  A  E  G  Q  R  K  R  R  N  T  I  H    40

121  GAATTCAAAAAATCAGCAAAGACTACCCTAATCAAAATAGATCCAGCACTGAAGATAAAA
     ------------+---------+---------+---------+---------+---------+ 180
     CTTAAGTTTTTTAGTCGTTTCTGATGGGATTAGTTTTATCTAGGTCGTGACTTCTATTTT

41  E  F  K  K  S  A  K  T  T  L  I  K  I  D  P  A  L  K  I  K    60

181  ACCAAAAAAGTGAATACTGCAGACCAATGTGCTAATAGATGTACTAGGAATAAAGGACTT
     ------------+---------+---------+---------+---------+---------+ 240
     TGGTTTTTTCACTTATGACGTCTGGTTACACGATTATCTACATGATCCTTATTTCCTGAA

61  T  K  K  V  N  T  A  D  Q  C  A  N  R  C  T  R  N  K  G  L    80

241  CCATTCACTTGCAAGGCTTTTGTTTTTGATAAAGCAAGAAAACAATGCCTCTGGTTCCCC
     ------------+---------+---------+---------+---------+---------+ 300
     GGTAAGTGAACGTTCCGAAAACAAAAACTATTTCGTTCTTTTGTTACGGAGACCAAGGGG

81  P  F  T  C  K  A  F  V  F  D  K  A  R  K  Q  C  L  W  F  P   100

301  TTCAATAGCATGTCAAGTGGAGTGAAAAAAGAATTTGGCCATGAATTTGACCTCTATGAA
     ------------+---------+---------+---------+---------+---------+ 360
     AAGTTATCGTACAGTTCACCTCACTTTTTTCTTAAACCGGTACTTAAACTGGAGATACTT

101  F  N  S  M  S  S  G  V  K  K  E  F  G  H  E  F  D  L  Y  E   120

361  AACAAAGACTACATTAGAAACTGCATCATTGGTAAAGGACGCAGCTACAAGGGAACAGTA
     ------------+---------+---------+---------+---------+---------+ 420
     TTGTTTCTGATGTAATCTTTGACGTAGTAACCATTTCCTGCGTCGATGTTCCCTTGTCAT

121  N  K  D  Y  I  R  N  C  I  I  G  K  G  R  S  Y  K  G  T  V   140

421  TCTATCACTAAGAGTGGCATCAAATGTCAGCCCTGGAGTTCCATGATACCACACGAACAC
     ------------+---------+---------+---------+---------+---------+ 480
     AGATAGTGATTCTCACCGTAGTTTACAGTCGGGACCTCAAGGTACTATGGTGTGCTTGTG

141  S  I  T  K  S  G  I  K  C  Q  P  W  S  S  M  I  P  H  E  H   160

481  AGCTATCGGGGTAAAGACCTACAGGAAAACTACTGTCGAAATCCTCGAGGGGAAGAAGGG
     ------------+---------+---------+---------+---------+---------+ 540
     TCGATAGCCCCATTTCTGGATGTCCTTTTGATGACAGCTTTAGGAGCTCCCCTTCTTCCC

161  S  Y  R  G  K  D  L  Q  E  N  Y  C  R  N  P  R  G  E  E  G   180
```

(continued)

(continued)

```
       GGACCCTGGTGTTTCACAAGCAATCCAGAGGTACGCTACGAAGTCTGTGACATTCCTCAG
541    ------------------------------------------------------------  600
       CCTGGGACCACAAAGTGTTCGTTAGGTCTCCATGCGATGCTTCAGACACTGTAAGGAGTC
181     G  P  W  C  F  T  S  N  P  E  V  R  Y  E  V  C  D  I  P  Q  200

TGTTCAGAAGTTGAATGCATGACCTGCAATGGGGAGAGTTATCGAGGTCTCATGGATCAT
601    ------------------------------------------------------------  660
       ACAAGTCTTCAACTTACGTACTGGACGTTACCCCTCTCAATAGCTCCAGAGTACCTAGTA
201     C  S  E  V  E  C  M  T  C  N  G  E  S  Y  R  G  L  M  D  H  220

ACAGAATCAGGCAAGATTTGTCAGCGCTGGGATCATCAGACACCACACCGGCACAAATTC
661    ------------------------------------------------------------  720
       TGTCTTAGTCCGTTCTAAACAGTCGCGACCCTAGTAGTCTGTGGTGTGGCCGTGTTTAAG
221     T  E  S  G  K  I  C  Q  R  W  D  H  Q  T  P  H  R  H  K  F  240

TTGCCTGAAAGATATCCCGACAAGGGCTTTGATGATAATTATTGCCGCAATCCCGATGGC
721    ------------------------------------------------------------  780
       AACGGACTTTCTATAGGGCTGTTCCCGAAACTACTATTAATAACGGCGTTAGGGCTACCG
241     L  P  E  R  Y  P  D  K  G  F  D  D  N  Y  C  R  N  P  D  G  260

CAGCCGAGGCCATGGTGCTATACTCTTGACCCTCACACCCGCTGGGAGTACTGTGCAATT
781    ------------------------------------------------------------  840
       GTCGGCTCCGGTACCACGATATGAGAACTGGGAGTGTGGGCGACCCTCATGACACGTTAA
261     Q  P  R  P  W  C  Y  T  L  D  P  H  T  R  W  E  Y  C  A  I  280

AAAACATGCGCTGACAATACTATGAATGACACTGATGTTCCTTTGGAAACAACTGAATGC
841    ------------------------------------------------------------  900
       TTTTGTACGCGACTGTTATGATACTTACTGTGACTACAAGGAAACCTTTGTTGACTTACG
281     K  T  C  A  D  N  T  M  N  D  T  D  V  P  L  E  T  T  E  C  300

ATCCAAGGTCAAGGAGAAGGCTACAGGGGCACTGTCAATACCATTTGGAATGGAATTCCA
901    ------------------------------------------------------------  960
       TAGGTTCCAGTTCCTCTTCCGATGTCCCCGTGACAGTTATGGTAAACCTTACCTTAAGGT
301     I  Q  G  Q  G  E  G  Y  R  G  T  V  N  T  I  W  N  G  I  P  320

TGTCAGCGTTGGGATTCTCAGTATCCTCACGAGCATGACATGACTCCTGAAAATTTCAAG
961    ------------------------------------------------------------  1020
       ACAGTCGCAACCCTAAGAGTCATAGGAGTGCTCGTACTGTACTGAGGACTTTTAAAGTTC
321     C  Q  R  W  D  S  Q  Y  P  H  E  H  D  M  T  P  E  N  F  K  340

TGCAAGGACCTACGAGAAAATTACTGCCGAAATCCAGATGGGTCTGAATCACCCTGGTGT
1021   ------------------------------------------------------------  1080
       ACGTTCCTGGATGCTCTTTTAATGACGGCTTTAGGTCTACCCAGACTTAGTGGGACCACA
341     C  K  D  L  R  E  N  Y  C  R  N  P  D  G  S  E  S  P  W  C  360

TTTACCACTGATCCAAACATCCGAGTTGGCTACTGCTCCCAAATTCCAAACTGTGATATG
1081   ------------------------------------------------------------  1140
       AAATGGTGACTAGGTTTGTAGGCTCAACCGATGACGAGGGTTTAAGGTTTGACACTATAC
361     F  T  T  D  P  N  I  R  V  G  Y  C  S  Q  I  P  N  C  D  M  380

TCACATGGACAAGATTGTTATCGTGGGAATGGCAAAAATTATATGGGCAACTTATCCCAA
1141   ------------------------------------------------------------  1200
       AGTGTACCTGTTCTAACAATAGCACCCTTACCGTTTTTAATATACCCGTTGAATAGGGTT
381     S  H  G  Q  D  C  Y  R  G  N  G  K  N  Y  M  G  N  L  S  Q  400

ACAAGATCTGGACTAACATGTTCAATGTGGGACAAGAACATGGAAGACTTACATCGTCAT
1201   ------------------------------------------------------------  1260
       TGTTCTAGACCTGATTGTACAAGTTACACCCTGTTCTTGTACCTTCTGAATGTAGCAGTA
401     T  R  S  G  L  T  C  S  M  W  D  K  N  M  E  D  L  H  R  H  420
```

(continued)

(continued)

```
       ATCTTCTGGGAACCAGATGCAAGTAAGCTGAATGAGAATTACTGCCGAAATCCAGATGAT
1261   ------------------------------------------------------------  1320
       TAGAAGACCCTTGGTCTACGTTCATTCGACTTACTCTTAATGACGGCTTTAGGTCTACTA

421    I  F  W  E  P  D  A  S  K  L  N  E  N  Y  C  R  N  P  D  D   440

GACGCTCATGGACCCTGGTGCTACACGGGAAATCCACTCATTCCTTGGGATTATTGCCCT
1321   ------------------------------------------------------------  1380
       CTGCGAGTACCTGGGACCACGATGTGCCCTTTAGGTGAGTAAGGAACCCTAATAACGGGA

441    D  A  H  G  P  W  C  Y  T  G  N  P  L  I  P  W  D  Y  C  P   460

ATTTCTCGTTGTGAAGGTGATACCACACCTACAATAGTCAATTTAGACCATCCCGTAATA
1381   ------------------------------------------------------------  1440
       TAAAGAGCAACACTTCCACTATGGTGTGGATGTTATCAGTTAAATCTGGTAGGGCATTAT

461    I  S  R  C  E  G  D  T  T  P  T  I  V  N  L  D  H  P  V  I   480

TCTTGTGCCAAAACGAAACAATTGCGA
1441   ---------------------------  1467    (End of the sequence
       AGAACACGGTTTTGCTTTGTTAACGCT           derived from HGF)

481     S  C  A  K  T  K  Q  L  R    489
```

(Start of the sequence derived from MSP)

```
                GTGGTTGGGGGCCATCCGGGCAACTCACCCTGGACAGTCAGCTTGCGGAAT
        1468    --------------------------------------------------  1518
                CACCAACCCCCGGTAGGCCCGTTGAGTGGGACCTGTCAGTCGAACGCCTTA

490    V  V  G  G  H  P  G  N  S  P  W  T  V  S  L  R  N     506

CGGCAGGGCCAGCATTTCTGCGGGGGGTCTCTAGTGAAGGAGCAGTGGATACTGACTGCC
1519   ------------------------------------------------------------  1560
       GCCGTCCCGGTCGTAAAGACGCCCCCAGAGATCACTTCCTCGTCACCTATGACTGACGG

507    R  Q  G  Q  H  F  C  G  G  S  L  V  K  E  Q  W  I  L  T  A   526

CGGCAGTGCTTCTCCTCCTGCCATATGCCTCTCACGGGCTATGAGGTATGGTTGGGCACC
1561   ------------------------------------------------------------  1620
       GCCGTCACGAAGAGGAGGACGGTATACGGAGAGTGCCCGATACTCCATACCAACCCGTGG

521    R  Q  C  F  S  S  C  H  M  P  L  T  G  Y  E  V  W  L  G  T   546

CTGTTCCAGAACCCACAGCATGGAGAGCCAAGCCTACAGCGGGTCCCAGTAGCCAAGATG
1621   ------------------------------------------------------------  1680
       GACAAGGTCTTGGGTGTCGTACCTCTCGGTTCGGATGTCGCCCAGGGTCATCGGTTCTAC

541    L  F  Q  N  P  Q  H  G  E  P  S  L  Q  R  V  P  V  A  K  M   566

GTGTGTGGGCCCTCAGGCTCCCAGCTTGTCCTGCTCAAGCTGGAGAGATCTGTGACCCTG
1681   ------------------------------------------------------------  1740
       CACACACCCGGGAGTCCGAGGGTCGAACAGGACGAGTTCGACCTCTCTAGACACTGGGAC

561    V  C  G  P  S  G  S  Q  L  V  L  L  K  L  E  R  S  V  T  L   586

AACCAGCGTGTGGCCCTGATCTGCCTGCCCCCTGAATGGTATGTGGTGCCTCCAGGGACC
1741   ------------------------------------------------------------  1800
       TTGGTCGCACACCGGGACTAGACGGACGGGGGACTTACCATACACCACGGAGGTCCCTGG

581    N  Q  R  V  A  L  I  C  L  P  P  E  W  Y  V  V  P  P  G  T   606

AAGTGTGAGATTGCAGGCTGGGGTGAGACCAAAGGTACGGGTAATGACACAGTCCTAAAT
1801   ------------------------------------------------------------  1860
       TTCACACTCTAACGTCCGACCCCACTCTGGTTTCCATGCCCATTACTGTGTCAGGATTTA

601    K  C  E  I  A  G  W  G  E  T  K  G  T  G  N  D  T  V  L  N   626

GTGGCCTTTCTGAATGTTATCTCCAACCAGGAGTGTAACATCAAGCACCGAGGACGTGTG
1861   ------------------------------------------------------------  1920
       CACCGGAAAGACTTACAATAGAGGTTGGTCCTCACATTGTAGTTCGTGGCTCCTGCACAC
```

(continued)

(continued)

```
 621  V  A  F  L  N  V  I  S  N  Q  E  C  N  I  K  H  R  G  R  V    645

1921  CGGGAGAGTGAGATGTGCACTGAGGGACTGTTGGCCCCTGTGGGGGCCTGTGAGGGTGAC
      ------------+---------+---------+---------+---------+---------+  1980
      GCCCTCTCACTCTACACGTGACTCCCTGACAACCGGGGACACCCCCGGACACTCCCACTG

641  R  E  S  E  M  C  T  E  G  L  L  A  P  V  G  A  C  E  G  D    666

1981  TACGGGGGCCCACTTGCCTGCTTTACCCACAACTGCTGGGTCCTGGAAGGAATTATAATC
      ------------+---------+---------+---------+---------+---------+  2040
      ATGCCCCCGGGTGAACGGACGAAATGGGTGTTGACGACCCAGGACCTTCCTTAATATTAG

661  Y  G  G  P  L  A  C  F  T  H  N  C  W  V  L  E  G  I  I  I    686

2041  CCCAACCGAGTATGCGCAAGGTCCCGCTGGCCAGCTGTCTTCACGCGTGTCTCTGTGTTT
      ------------+---------+---------+---------+---------+---------+  2100
      GGGTTGGCTCATACGCGTTCCAGGGCGACCGGTCGACAGAAGTGCGCACAGAGACACAAA

681  P  N  R  V  C  A  R  S  R  W  P  A  V  F  T  R  V  S  V  F    706

2101  GTGGACTGGATTCACAAGGTCATGAGACTGGGTTAG
      ------------+---------+---------+---              2136
      CACCTGACCTAAGTGTTCCAGTACTCTGACCCAATC

701  V  D  W  I  H  K  V  M  R  L  G  *    711
```

Figure 3A:
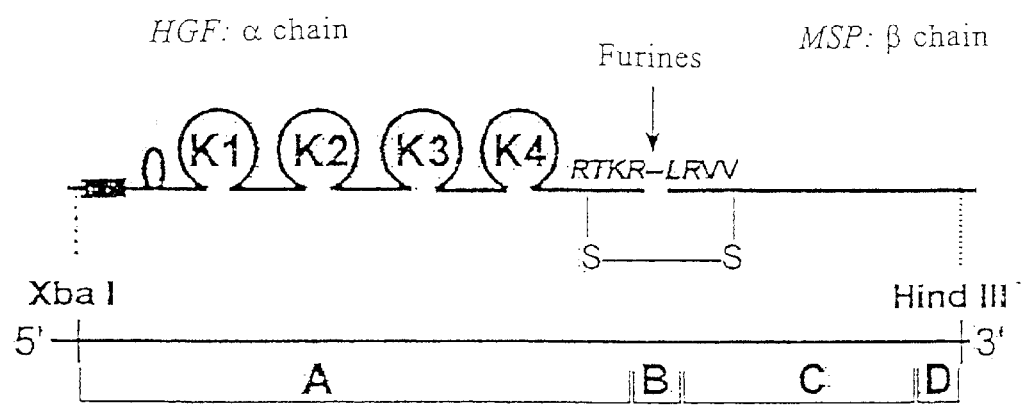

FIGURE 3b

```
      ATGTGGGTGACCAAACTCCTGCCAGCCCTGCTGCTGCAGCATGTCCTCCTGCATCTCCTC
  1   ------------------------------------------------------------   60
      TACACCCACTGGTTTGAGGACGGTCGGGACGACGACGTCGTACAGGAGGACGTAGAGGAG

1   M  W  V  T  K  L  L  P  A  L  L  L  Q  H  V  L  L  H  L  L    20

CTGCTCCCCATCGCCATCCCCTATGCAGAGGGACAAAGGAAAAGAAGAAATACAATTCAT
 61   ------------------------------------------------------------   120
      GACGAGGGGTAGCGGTAGGGGATACGTCTCCCTGTTTCCTTTTCTTCTTTATGTTAAGTA

21   L  L  P  I  A  I  P  Y  A  E  G  Q  R  K  R  R  N  T  I  H    40

GAATTCAAAAAATCAGCAAAGACTACCCTAATCAAAATAGATCCAGCACTGAAGATAAAA
121   ------------------------------------------------------------   180
      CTTAAGTTTTTTAGTCGTTTCTGATGGGATTAGTTTTATCTAGGTCGTGACTTCTATTTT

41   E  F  K  K  S  A  K  T  T  L  I  K  I  D  P  A  L  K  I  K    60

ACCAAAAAAGTGAATACTGCAGACCAATGTGCTAATAGATGTACTAGGAATAAAGGACTT
181   ------------------------------------------------------------   240
      TGGTTTTTTCACTTATGACGTCTGGTTACACGATTATCTACATGATCCTTATTTCCTGAA

61   T  K  K  V  N  T  A  D  Q  C  A  N  R  C  T  R  N  K  G  L    80

CCATTCACTTGCAAGGCTTTTGTTTTTGATAAAGCAAGAAAACAATGCCTCTGGTTCCCC
241   ------------------------------------------------------------   300
      GGTAAGTGAACGTTCCGAAAACAAAAACTATTTCGTTCTTTTGTTACGGAGACCAAGGGG

81   P  F  T  C  K  A  F  V  F  D  K  A  R  K  Q  C  L  W  F  P    100

TTCAATAGCATGTCAAGTGGAGTGAAAAAAGAATTTGGCCATGAATTTGACCTCTATGAA
301   ------------------------------------------------------------   360
      AAGTTATCGTACAGTTCACCTCACTTTTTCTTAAACCGGTACTTAAACTGGAGATACTT

101   F  N  S  M  S  S  G  V  K  K  E  F  G  H  E  F  D  L  Y  E    120

AACAAAGACTACATTAGAAACTGCATCATTGGTAAAGGACGCAGCTACAAGGGAACAGTA
361   ------------------------------------------------------------   420
      TTGTTTCTGATGTAATCTTTGACGTAGTAACCATTTCCTGCGTCGATGTTCCCTTGTCAT

121   N  K  D  Y  I  R  N  C  I  I  G  K  G  R  S  Y  K  G  T  V    140

TCTATCACTAAGAGTGGCATCAAATGTCAGCCCTGGAGTTCCATGATACCACACGAACAC
421   ------------------------------------------------------------   480
      AGATAGTGATTCTCACCGTAGTTTACAGTCGGGACCTCAAGGTACTATGGTGTGCTTGTG

141   S  I  T  K  S  G  I  K  C  Q  P  W  S  S  M  I  P  H  E  H    160

AGCTATCGGGGTAAAGACCTACAGGAAAACTACTGTCGAAATCCTCGAGGGGAAGAAGGG
481   ------------------------------------------------------------   540
      TCGATAGCCCCATTTCTGGATGTCCTTTTGATGACAGCTTTAGGAGCTCCCCTTCTTCCC

161   S  Y  R  G  K  D  L  Q  E  N  Y  C  R  N  P  R  G  E  E  G    180
```

(continued)

(continued)

```
     GGACCCTGGTGTTTCACAAGCAATCCAGAGGTACGCTACGAAGTCTGTGACATTCCTCAG
541  ------------------------------------------------------------  600
     CCTGGGACCACAAAGTGTTCGTTAGGTCTCCATGCGATGCTTCAGACACTGTAAGGAGTC

181  G  P  W  C  F  T  S  N  P  E  V  R  Y  E  V  C  D  I  P  Q   200

TGTTCAGAAGTTGAATGCATGACCTGCAATGGGGAGAGTTATCGAGGTCTCATGGATCAT
601  ------------------------------------------------------------  660
     ACAAGTCTTCAACTTACGTACTGGACGTTACCCCTCTCAATAGCTCCAGAGTACCTAGTA

201  C  S  E  V  E  C  M  T  C  N  G  E  S  Y  R  G  L  M  D  H   220

ACAGAATCAGGCAAGATTTGTCAGCGCTGGGATCATCAGACACCACACCGGCACAAATTC
661  ------------------------------------------------------------  720
     TGTCTTAGTCCGTTCTAAACAGTCGCGACCCTAGTAGTCTGTGGTGTGGCCGTGTTTAAG

221  T  E  S  G  K  I  C  Q  R  W  D  H  Q  T  P  H  R  H  K  F   240

TTGCCTGAAAGATATCCCGACAAGGGCTTTGATGATAATTATTGCCGCAATCCCGATGGC
721  ------------------------------------------------------------  780
     AACGGACTTTCTATAGGGCTGTTCCCGAAACTACTATTAATAACGGCGTTAGGGCTACCG

241  L  P  E  R  Y  P  D  K  G  F  D  D  N  Y  C  R  N  P  D  G   260

CAGCCGAGGCCATGGTGCTATACTCTTGACCCTCACACCCGCTGGGAGTACTGTGCAATT
781  ------------------------------------------------------------  840
     GTCGGCTCCGGTACCACGATATGAGAACTGGGAGTGTGGGCGACCCTCATGACACGTTAA

261  Q  P  R  P  W  C  Y  T  L  D  P  H  T  R  W  E  Y  C  A  I   280

AAAACATGCGCTGACAATACTATGAATGACACTGATGTTCCTTTGGAAACAACTGAATGC
841  ------------------------------------------------------------  900
     TTTTGTACGCGACTGTTATGATACTTACTGTGACTACAAGGAAACCTTTGTTGACTTACG

281  K  T  C  A  D  N  T  M  N  D  T  D  V  P  L  E  T  T  E  C   300

ATCCAAGGTCAAGGAGAAGGCTACAGGGGCACTGTCAATACCATTTGGAATGGAATTCCA
901  ------------------------------------------------------------  960
     TAGGTTCCAGTTCCTCTTCCGATGTCCCCGTGACAGTTATGGTAAACCTTACCTTAAGGT

301  I  Q  G  Q  G  E  G  Y  R  G  T  V  N  T  I  W  N  G  I  P   320

TGTCAGCGTTGGGATTCTCAGTATCCTCACGAGCATGACATGACTCCTGAAAATTTCAAG
961  ------------------------------------------------------------  1020
     ACAGTCGCAACCCTAAGAGTCATAGGAGTGCTCGTACTGTACTGAGGACTTTTAAAGTTC

321  C  Q  R  W  D  S  Q  Y  P  H  E  H  D  M  T  P  E  N  F  K   340

TGCAAGGACCTACGAGAAAATTACTGCCGAAATCCAGATGGGTCTGAATCACCCTGGTGT
1021  -----------------------------------------------------------  1080
      ACGTTCCTGGATGCTCTTTTAATGACGGCTTTAGGTCTACCCAGACTTAGTGGGACCACA

341  C  K  D  L  R  E  N  Y  C  R  N  P  D  G  S  E  S  P  W  C   360

TTTACCACTGATCCAAACATCCGAGTTGGCTACTGCTCCCAAATTCCAAACTGTGATATG
1081  -----------------------------------------------------------  1140
      AAATGGTGACTAGGTTTGTAGGCTCAACCGATGACGAGGGTTTAAGGTTTGACACTATAC

361  F  T  T  D  P  N  I  R  V  G  Y  C  S  Q  I  P  N  C  D  M   380

TCACATGGACAAGATTGTTATCGTGGGAATGGCAAAAATTATATGGGCAACTTATCCCAA
1141  -----------------------------------------------------------  1200
      AGTGTACCTGTTCTAACAATAGCACCCTTACCGTTTTTAATATACCCGTTGAATAGGGTT

381  S  H  G  Q  D  C  Y  R  G  N  G  K  N  Y  M  G  N  L  S  Q   400

ACAAGATCTGGACTAACATGTTCAATGTGGGACAAGAACATGGAAGACTTACATCGTCAT
1201  -----------------------------------------------------------  1260
      TGTTCTAGACCTGATTGTACAAGTTACACCCTGTTCTTGTACCTTCTGAATGTAGCAGTA

401  T  R  S  G  L  T  C  S  M  W  D  K  N  M  E  D  L  H  R  H   420
```

(continued)

(continued)

```
1261 ATCTTCTGGGAACCAGATGCAAGTAAGCTGAATGAGAATTACTGCCGAAATCCAGATGAT
     ------------+---------+---------+---------+---------+---------
     TAGAAGACCCTTGGTCTACGTTCATTCGACTTACTCTTAATGACGGCTTTAGGTCTACTA  1320

421  I  F  W  E  P  D  A  S  K  L  N  E  N  Y  C  R  N  P  D  D   440

1321 GACGCTCATGGACCCTGGTGCTACACGGGAAATCCACTCATTCCTTGGGATTATTGCCCT
     ------------+---------+---------+---------+---------+---------
     CTGCGAGTACCTGGGACCACGATGTGCCCTTTAGGTGAGTAAGGAACCCTAATAACGGGA  1380

441  D  A  H  G  P  W  C  Y  T  G  N  P  L  I  P  W  D  Y  C  P   460

1381 ATTTCTCGTTGTGAAGGTGATACCACACCTACAATAGTCAATTTAGACCATCCCGTAATA
     ------------+---------+---------+---------+---------+---------
     TAAAGAGCAACACTTCCACTATGGTGTGGATGTTATCAGTTAAATCTGGTAGGGCATTAT  1440

461  I  S  R  C  E  G  D  T  T  P  T  I  V  N  L  D  H  P  V  I   480

1441 TCTTGTGCCAGAACGAAACGATTGCGA
     ------------+---------+     1467   (End of the sequence
     AGAACACGGTCTTGCTTTGCTAACGCT                derived from HGF)

481     S  C  A  R  T  K  R  L  R    489
```

```
(Beginning of the 1468 GTGGTTGGGGGCCATCCGGGCAACTCACCCTGGACAGTCAGCTTGCGGAAT
sequence derived        ------------+---------+---------+---------+---------
from MSP)               CACCAACCCCCGGTAGGCCCGTTGAGTGGGACCTGTCAGTCGAACGCCTTA  1518

490  V  V  G  G  H  P  G  N  S  P  W  T  V  S  L  R  N    506

1519 CGGCAGGGCCAGCATTTCTGCGGGGGGTCTCTAGTGAAGGAGCAGTGGATACTGACTGCC
     ------------+---------+---------+---------+---------+---------
     GCCGTCCCGGTCGTAAAGACGCCCCCCAGAGATCACTTCCTCGTCACCTATGACTGACGG  1560

507  R  Q  G  Q  H  F  C  G  G  S  L  V  K  E  Q  W  I  L  T  A   526

1561 CGGCAGTGCTTCTCCTCCTGCCATATGCCTCTCACGGGCTATGAGGTATGGTTGGGCACC
     ------------+---------+---------+---------+---------+---------
     GCCGTCACGAAGAGGAGGACGGTATACGGAGAGTGCCCGATACTCCATACCAACCCGTGG  1620

521  R  Q  C  F  S  S  C  H  M  P  L  T  G  Y  E  V  W  L  G  T   546

1621 CTGTTCCAGAACCCACAGCATGGAGAGCCAAGCCTACAGCGGGTCCCAGTAGCCAAGATG
     ------------+---------+---------+---------+---------+---------
     GACAAGGTCTTGGGTGTCGTACCTCTCGGTTCGGATGTCGCCCAGGGTCATCGGTTCTAC  1680

541  L  F  Q  N  P  Q  H  G  E  P  S  L  Q  R  V  P  V  A  K  M   566

1681 GTGTGTGGGCCCTCAGGCTCCCAGCTTGTCCTGCTCAAGCTGGAGAGATCTGTGACCCTG
     ------------+---------+---------+---------+---------+---------
     CACACACCCGGGAGTCCGAGGGTCGAACAGGACGAGTTCGACCTCTCTAGACACTGGGAC  1740

561  V  C  G  P  S  G  S  Q  L  V  L  L  K  L  E  R  S  V  T  L   586

1741 AACCAGCGTGTGGCCCTGATCTGCCTGCCCCCTGAATGGTATGTGGTGCCTCCAGGGACC
     ------------+---------+---------+---------+---------+---------
     TTGGTCGCACACCGGGACTAGACGGACGGGGACTTACCATACACCACGGAGGTCCCTGG  1800

581  N  Q  R  V  A  L  I  C  L  P  P  E  W  Y  V  V  P  P  G  T   606

1801 AAGTGTGAGATTGCAGGCTGGGGTGAGACCAAAGGTACGGGTAATGACACAGTCCTAAAT
     ------------+---------+---------+---------+---------+---------
     TTCACACTCTAACGTCCGACCCCACTCTGGTTTCCATGCCCATTACTGTGTCAGGATTTA  1860

601  K  C  E  I  A  G  W  G  E  T  K  G  T  G  N  D  T  V  L  N   626

1861 GTGGCCTTTCTGAATGTTATCTCCAACCAGGAGTGTAACATCAAGCACCGAGGACGTGTG
     ------------+---------+---------+---------+---------+---------
     CACCGGAAAGACTTACAATAGAGGTTGGTCCTCACATTGTAGTTCGTGGCTCCTGCACAC  1920
```

(continued)

(continued)

```
621  V  A  F  L  N  V  I  S  N  Q  E  C  N  I  K  H  R  G  R  V    646

CGGGAGAGTGAGATGTGCACTGAGGGACTGTTGGCCCCTGTGGGGGCCTGTGAGGGTGAC
1921  ------------+---------+---------+---------+---------+---------+  1980
      GCCCTCTCACTCTACACGTGACTCCCTGACAACCGGGGACACCCCCGGACACTCCCACTG

641  R  E  S  E  M  C  T  E  G  L  L  A  P  V  G  A  C  E  G  D    666

TACGGGGGCCCACTTGCCTGCTTTACCCACAACTGCTGGGTCCTGGAAGGAATTATAATC
1981  ------------+---------+---------+---------+---------+---------+  2040
      ATGCCCCCGGGTGAACGGACGAAATGGGTGTTGACGACCCAGGACCTTCCTTAATATTAG

661  Y  G  G  P  L  A  C  F  T  H  N  C  W  V  L  E  G  I  I  I    686

CCCAACCGAGTATGCGCAAGGTCCCGCTGGCCAGCTGTCTTCACGCGTGTCTCTGTGTTT
2041  ------------+---------+---------+---------+---------+---------+  2100
      GGGTTGGCTCATACGCGTTCCAGGGCGACCGGTCGACAGAAGTGCGCACAGAGACACAAA

681  P  N  R  V  C  A  R  S  R  W  P  A  V  F  T  R  V  S  V  F    706

GTGGACTGGATTCACAAGGTCATGAGACTGGGTTAG
2101  ------------+---------+---------+------  2136
      CACCTGACCTAAGTGTTCCAGTACTCTGACCCAATC

701  V  D  W  I  H  K  V  M  R  L  G  *                             711
```

RECOMBINANT PROTEINS FROM HGF AND MSP

This application is the national phase under 35 U.S.C. §371 of PCT International Application No. PCT/EP99/00502 which has an International filing date of Jan. 28, 1999, which designated the United States of America.

FIELD OF THE INVENTION

The present invention relates to recombinant proteins obtained from the combination of structural domains derived from the α subunits of hepatocyte growth factor (HGF) and macrophage stimulating protein (MSP).

In particular, the engineered factors of the invention are obtained by combining the hairpin loop and kringle domains of HGF α chains and/or MSP, together with HGF or MSP β chains, to obtain a structure having two superdomains joined by an intervening linker sequence. Moreover, the invention relates to DNA sequences encoding the above mentioned recombinant proteins, to the expression vectors comprising said DNA sequences and to host cells containing said expression vectors. The recombinant proteins of the present invention are biologically active and protect epithelial cells and other cells from apoptosis induced by chemotherapic drugs. Therefore, these molecules can conveniently be used to prevent or treat the toxic side effects of the chemotherapeutical treatment of tumours.

STATE OF THE ART

Hepatocyte Growth Factor (HGF) and Macrophage Stimulating Protein (MSP) are highly related proteins both structurally and functionally (FIGS. 1 and 2). Both these factors are secreted as an inactive precursor, which is processed by specific proteases which recognise a cleavage site inside the molecule, dividing the protein in two subunits. These subunits, named α chain and β chain, are linked by a disulphide bond. Thus, the mature factor is an α-β dimeric protein. Only the mature (dimeric) form of the factor is able to activate its receptor at the surface of the target cells (the Met tyrosine kinase in the case of HGF and the Ron tyrosine kinase in the case of MSP) and therefore to mediate biological responses (Naldini, L. et al., 1992, EMBO J. 11: 4825–4833; Wang, M. et al., 1994, J. Biol. Chem. 269; 3436–3440; Bottaro, D. et al., 1991, Science 25: 802–804; Naldini, L. et al., 1991, EMBO J. 10: 2867–2878; Wang, M. et al., 1994, Science 266: 117–119; Gaudino, G. et al., 1994, EMBO J. 13: 3524–3532).

The α chain of both factors contains a hairpin loop (HL) structure and four domains with a tangle-like structure named kringles (K1–K4; Nakamura, T. et al., 1989, Nature 342: 440–443; Han, S. et al., 1991, Biochemistry 30: 9768–9780). The precursor also contains a signal sequence (LS) of 31 amino acids (in the case of HGF) or of 18 amino acids (in the case of MSP), removed in rough endoplasmic reticulum, which directs the neoformed peptide to the secretive pathway. The β chain contains a sequence box homologous to the typical catalytic domain of serine proteases, but it has no enzymatic activity (Nakamura, T. et al., 1989, Nature 342:440–443; Han, S. et al., 1991, Biochemistry 30:9768–9780). Both α and β chains contribute to the binding of the growth factor to the respective receptor (Met for HGF and Ron for MSP).

HGF and MSP polypeptides are able to induce a variety of biological effects besides cell proliferation. The main biological activities of these molecules are: stimulation of cell division (mitogenesis); stimulation of motility (scattering); induction of polarisation and cell differentiation; induction of tubule formation (branched morphogenesis), increase of cell survival (protection from apoptosis). The tissues that respond to HGF and MSP stimulation are those containing cells that express the respective Met (HGF) and Ron (MSP) receptors. The most important target tissues of these factors are epithelia of different organs, such as liver, kidney, lung, breast, pancreas and stomach, and some cells of the hematopoietic and nervous systems. A detailed review of the biological effects of HGF and MSP in the various tissues can he found in: Tamagnone, L. & Comoglio, P., Cytokine & Growth Factor Reviews, 1997, 8: 129–142, Elsevier Science Ltd.; Zarnegar, R. & Michalopoulos, G., 1995, J. Cell Biol. 129: 1177–1180; Medico, E. et al., 1996, Mol. Biol. Cell, 7: 495–504; Banu, N. et al., 1996, J. Immunol. 156: S2933–2940.

In the case of HGF, the hairpin loop and the first two kringles are known to contain the sites of direct interaction with the Met receptor (Lokker, N. et al., 1992, EMBO J. 11: 2503–251.0; Lokker, N. et al., 1994, Protein Engineering 7: 895–903). Two naturally-occurring truncated forms of HGF produced by some cells by alternative splicing have been described. The first one comprises the first kringle (NK1-HGF Cioce, V. et al., 1996, J. Biol. Chem. 271: 13110–13115) whereas the second one spans to the second kringle (NK2-HGF Miyazawa, K. et al., 1991, Eur. J. Biochem. 197: 15–22). NK2-HGF induces cell scattering, but it is not mitogenic as the complete growth factor is (Hartmann, G. et al., 1992, Proc. Natl. Acad. Sci. USA 89: 11574–11578). However, NK2-HGF exhibits mitocenic activity in the presence of heparin, a glycosaminoglycan that binds the first kringle of HGF and is likely to induce dimerization of NK2-HGF (Schwall, R. et al., 1996, J. Cell Biol. 133: 709–718). Moreover NK2-HGF, being a partial agonist of Met, behaves as a competitive inhibitor of HGF as far as the mitogenic activity is concerned (Chan, A. et al., 1991, Science 254: 1382–1385). NK1-HGF has also been described to exert partial stimulation of Met and competitive inhibition of HGF mitogenic activity (Cioce, V. et al., 1996, J. Biol. Chem. 271: 13110–13115).

In the case of MSP, the modality of interaction with the Ron receptor is less understood: some preliminary studies suggest a situation opposite of that of HGF, i.e. the β chain directly binds the receptor whereas the α chain stabilises the complex (Wang, M. et al., 1997, J. Biol. Chem. 272: 16999–17004).

The therapeutical use of molecules such as HGF and MSP is potentially valuable in a wide range of pathologies (Abdulla, S., 1997, Mol. Med. Today 3: 233). Nevertheless, a number of technical as well as biological complications make the application of these molecules in clinics difficult.

For example, HGF was shown to protect kidney cells against programmed cell death (apoptosis) induced by cisplatinum, but at the same time it can induce an undesired proliferation of neoplastic cells. The natural truncated forms NK1 and NK2 of HGF show no problems of proteolytic activation, but they have a reduced biological activity.

SUMMARY OF THE INVENTION

The present invention provides recombinant molecules deriving from the combination of structural domains of HGF and MSP α and β subunits, which overcome the problems of the prior art molecules described above.

The molecules of the invention are composed of two superdomains, one obtained combining HL and K1–K4 domains of HGF and MSP α chains, the other corresponding to HGF or MSP β chain, connected by a linker which may contain a proteolytic cleavage site. This structure allows the recombinant proteins to interact with both Met and Ron receptors, in order to induce biological responses which are synergistic and selective compared with the natural factor and the truncated forms of the prior art.

DETAILED DISCLOSURE OF THE INVENTION

The present invention relates to recombinant proteins (which will be hereinafter referred to indifferently as proteins, molecules, engineered or recombinant factors) characterised by a structure that comprises two superdomains, one consisting of a combination of HL and K1–K4 domains derived from HGF or MSP α chain, the other corresponding to HGF or MSP β chain, linked by a spacer sequence or a linker. In particular, the invention relates to proteins of general formula (I)

[A]-B-[C]-(D)$_y$  (I)

in which

[A] corresponds to the sequence (LS)$_m$-HL-K1-(K2)$_n$-(K3)$_o$-(K4)$_p$ wherein (the numbering of the following amino acids being referred to the HGF and MSP sequences as reported in FIG. 1 and 2, respectively):

LS is an amino acid sequence corresponding to residues 1–31 of HGF or 1–18 of MSP;

HL is an amino acid sequence derived from the α chain of HGF starting between residues 32–70 and ending between residues 96–127; or it is an amino acid sequence derived from the α chain of MSP starting between residues 19–56 and ending between residues 78–109;

K1 is an amino acid sequence derived from the α chain of HGF starting between residues 97–128 and ending between residues 201–205; or it is an amino acid sequence derived from the α chain of MSP starting between residues 79–110 and ending between residues 186–190;

K2 is an amino acid sequence derived from the α chain of HGF starting between residues 202–206 and ending between residues 283–299; or it is an amino acid sequence derived from the α chain of MSP starting between residues 187–191 and ending between residues 268–282;

K3 is an amino acid sequence derived from the α chain of HGF starting between residues 284–300 and ending between residues 378–385; or it is an amino acid sequence derived from the α chain of MSP starting between residues 269–283 and ending between residues 361–369;

K4 is an amino acid sequence derived from the α chain of HGF starting between residues 379–386 and ending between residues 464–487; or it is an amino acid sequence derived from the α chain of MSP starting between residues 362–370 and ending between residues 448–481;

m, n, o, p is 0 or 1;

the sum n+o+p is an integer from 1 to 3 or 0, with the proviso that n≧o≧p;

B is selected from the sequence 488–491 of HGF, the sequence 478–489 of MSP, optionally preceded by a spacer of 1 to 13 aminoacids, a consensus sequence for protease or an uncleavable sequence;

[C] is the sequence of HGF β chain starting between amino acid residues 5 490 to 492 and ending at residue 723; or it is the sequence of MSP β chain starting between amino acid residues 484 to 486 and ending at residue 711; with the proviso that, when [A] coincides with HGF or MSP α chain, [C] corresponds to MSP and HGF β chain, respectively;

D is the sequence W–Z, wherein W is a conventional proteolytic site, Z any sequence useful for the purification of the protein on nickel or affinity columns; y is 0 or 1.

Non-limiting examples of W are consensus sequences for enterokinase protease, thrombin, factor Xa and IgA protease.

Preferred proteins of general formula (I), are those in which: HL domain is the sequence of HGF α chain ranging from amino acids 32 to 127, or the sequence of MPS α chain ranging from amino acids 19 to 98; K1 domain is the sequence of HGF α chain ranging from amino acids 128 to 203, or the sequence of MPS α chain ranging from amino acids 99 to 188; K2 domain is the sequence of HGF α chain ranging from amino acids 204 to 294, or the sequence of MPS α chain ranging from amino acids 189 to 274; K3 domain is the sequence of HGF α chain ranging from amino acids 286 to 383, or the sequence of MPS α chain ranging from amino acids 275 and 367; K4 domain is the sequence of HGF α chain ranging from amino acids 384 to 487, or the sequence of MPS α chain ranging from amino acids 368 and 477; C is the sequence 492–723 of HGF β chain, or the sequence 486–711 of MSP β chain.

Among the possible combinations of the domains of general formula (I), the following (II) and (III) are preferred, concerning two recombinant factors named Alphabet-1 and Alphabet-RTKR, respectively:

LS$_{HGF}$-HL$_{HGF}$-K1$_{HGF}$-K2$_{HGF}$-K3$_{HGF}$-K4$_{HGF}$-B$_{HGF}$-C$_{β_{MSP}}$-D    II (Alphabet 1)

LS$_{HGF}$-HL$_{HGF}$-K1$_{HGF}$-K2$_{HGF}$-K3$_{HGF}$-K4$_{HGF}$-B$_F$-C$_{β_{MSP}}$-D    III (Alphabet-RTKR)

wherein

LS$_{HGF}$-HL$_{HGF}$-K1$_{HGF}$-K2$_{HGF}$-K3$_{HGF}$-K4$_{HGF}$ is the sequence 1–487 of HGF, C$_{β_{MSP}}$ is the sequence 486–711 of MSP, D is the sequence GNSAVD(H)$_6$(SEQ ID NO:13).

In Alphabet-1 factor, B$_{HGF}$ is the sequence LRVV(SEQ ID NO:14), whereas for Alphabet-RTKR factor, B$_F$ is the sequence RTKR-LRVV(SEQ ID NO:15) (RTKR(SEQ ID NO:21) is the cleavage site for furine proteases).

The hybrid molecules of the invention are prepared by genetic engineering techniques according to a strategy involving the following steps:

a) construction of DNA encoding the desired protein;

b) insertion of DNA in an expression vector;

c) transformation of a host cell with recombinant DNA (rDNA);

d) culture of the transformed host cell so as to express the recombinant protein;

e) extraction and purification of the produced recombinant protein.

The DNA sequences corresponding to HGF or MSP structural domains can be obtained by synthesis or starting from DNA encoding for the two natural factors. For example, screening of cDNA libraries can be carried out using suitable probes, so as to isolate HGF or MSP cDNA. Alternatively, HGF or MSP cDNA can be obtained by reverse transcription from purified mRNA from suitable cells.

cDNAs coding for the fragments of HGF and MSP β chains can be amplificated by PCR (Mullis, K. B. and Faloona, F. A., Methods in Enzymol. 155 (1987) 335–350), and the amplification products can be recombined making use of suitable restriction sites, either naturally occurring in the factor sequences or artificially introduced in the oligonucleotide sequence used for the amplification.

In greater detail, one of the above mentioned strategies can be the following:

the portions of DNA encoding the LS, HL, K1, K2, K3 and K4 domains are amplificated by PCR from HGF or MSP cDNA and then recombined to obtain the hybrid sequences corresponding to [A] and [C]. Oligonucleotides recognising sequences located at the two ends of the domains to be amplificated are used as primers. Primers are designed so as to contain a sequence allowing recombination between the DNA of a domain and the adjacent one. Said recombination can be carried out by endonuclease cleavage and subsequent ligase reaction, or making use of the recombinant PCR method (Innis, NA et al., in PCR Protocols, Academic Press, 1990, 177–183).

Subsequently the cDNA portions encoding for the A and C domains are amplificated by PCR, wherein the antisense primer used to amplificate A and the sense primer used to amplificate C are hybrids, i.e. they contain both the 3'-end sequence of A and the 5'-end sequence of C. Between A and C is placed the domain B, a sequence which may encode a proteolytic cleavage site.

Two amplification products with an identical region artificially inserted are thereby obtained. The presence of this identical sequence allows the hybridisation of the two amplification products and thus the subsequent amplification of the recombinant construct containing the domains [A], B and C.

The amplificated recombinant construct containing the three domains [A], [B] and [C], is then inserted in a suitable vector. In this step it can be decided whether to add or not the domain D (tag), obtained by synthesis as a double strand oligonucleotide, downstream the domain C.

The recombinant expression vector can contain, in addition to the recombinant construct, a promoter, a ribosome binding site, an initiation codon, a stop codon, optionally a consensus site for expression enhancers.

The vector can also comprise a selection marker for isolating the host cells containing the DNA construct. Yeast or bacteria plasmids, such as plasmids suitable for *Escherichia Coli*, can be used as vectors, as well as bacteriophages, viruses, retroviruses, or DNA.

The vectors are cloned preferably in bacterial cells, for example in *Escherichia Coli*, as described in Maniatis, Molecular Cloning, Cold Spring Harbor Laboratory, New York, 1982, and the colonies can be selected, for example, by hybridisation with radiolabelled oligonucleotide probes; subsequently, the rDNA sequence extracted from the positive colonies is determined by known methods.

The vector with the recombinant construct can be introduced in the host cell according to the competent cell method, the protoplast method, the calcium phosphate method, the DEAE-dextran method, the electric impulses method, the in vitro packaging method, the viral vector method, the micro-injection method, or other suitable techniques.

Host cells can be prokaryotic or eukaryotic, such as bacteria, yeasts or mammal cells, and they will be such as to effectively produce the recombinant protein.

After transformation, cells are grown in a suitable medium, which can be for example MEM, DMEM or RPMI 1640 in the case of mammal host cells.

The recombinant protein is secreted in the culture medium from which it can be recovered and purified with different methods, such as mass exclusion, absorption, affinity chromatography, salting-out, precipitation, dialysis, ultrafiltration.

A simple, rapid system for the production of the molecules of the invention is, for example, transient expression in mammal cells.

Accordingly, the plasmid containing the recombinant DNA fragment, for example PMT2 (Sambrook, J. et al., Molecular Cloning, Cold Spring Harbor Laboratory Press, 1989), containing the recombinant DNA fragment, is transfected in suitable recipient cells, such as Cos7 (Sambrook, J. et al., supra) by the calcium phosphate technique or other equivalent techniques. Some days after transfection, the conditioned medium of the transfected cells is collected, cleared by centrifugation and analysed for its content in factor. For this analysis, antibodies directed against HGF or MSP, or against any tag sequence, can be used: the supernatant is immunoprecipitated and then analysed by western blot with the same antibody. The supernatant containing the recombinant factor can also be used directly for biochemical and biological tests. The protein can be purified, for example, if domain D is a poly-histidine tag sequence, by absorption on a nickel resin column and subsequent elution with imidazole.

The ability of the recombinant factors to bind both Met and Ron receptors, correctly synthesized and maturated in eukaryotic cells, has been tested. It has been found that hybrid factors containing HGF α chain and MSP β chain, i.e. the domains more directly involved in the binding with Met and Ron, respectively, are correctly synthesized by eukaryotic cells. The maturation (cleavage of the proteolytic site) takes place in the presence of serum, on a reduced but significant fraction of said proteins.

Moreover, it has been shown that the modification of the sequence of the proteolytic site permits the maturation of the hybrid factor also in the absence of serum.

Among the applications of the recombinant molecules of the invention, the following can be cited:

prevention of myelotoxicity; in particular they can be used for the expansion of marrow precursors, to increase proliferation of the hematopoietic precursors or to stimulate their entry in circle;

prevention of liver and kidney toxicity, and of mucositis following antineoplastic treatments; in particular the recombinant factors can be used to prevent toxicity (apoptosis) on differentiated cell elements of liver, kidney and mucosa of the gastroenteral tract, and to stimulate staminal elements of cutis and mucosas to allow the regeneration of germinative layers;

prevention of chemotherapeutic neurotoxicity.

In general, the proteins of the invention provide the following advantages, compared with the parent molecules HGF and MSP:

the capability of binding both Met and Ron receptors gives these molecules a wider activity;

by modification of the proteolytic site, hybrid factors can be obtained which are activated by proteases of the endoplasmic reticulum (such as furines), during their synthesis;

when the proteolytic site is removed, permanently immature forms of the factors can be obtained, having a potential partial agonistic or antagonistic activity;

the different functional domains can be combined so as to modulate the biological effects, increasing the favourable ones and reducing those undesired (for example, protection from apoptosis in favour of cell proliferation).

The invention has to be considered also directed at amino acid and nucleotide sequences referred to formula (I), having modifications which for example derive from degeneration of genetic code, without therefore modifying the amino acid sequence, or from the deletion, substitution, insertion, inversion or addition of nucleotides and/or bases according to all the possible methods known in the art.

Furthermore, the invention relates to the expression vectors comprising a sequence encoding for a protein of general formula (I), which can be plasmids, bacteriophages, viruses, retroviruses, or others, and to host cells containing said expression vectors.

Finally, the invention relates to the use of the recombinant proteins as therapeutical agents, and to pharmaceutical compositions containing an effective amount of the recombinant proteins together with pharmacologically acceptable excipients.

DESCRIPTION OF THE FIGURES (In the following, -His located after the name of the parent factors, truncated or recombinant, or of the plasmids, means that the respective sequences contain a poly-histidine tag).

FIG. 1:
a) Nucleotide(SEQ ID NO:9) and amino acid(SEQ ID NO:10) sequence of human HGF (Gene Bank #M73240; Weidner, K. M., et al., 1991, Proc. Acad. Sci. USA, 88:7001–7005). In contrast with the cited reference, in the numbering used herein, nucleotide No. 1 is the first base of the initiation codon (the A of the first ATG). The first amino acid is methionine. The cDNA untranslated regions at 5' and 3' are not represented neither considered in the numbering.

b) Nucleotide(SEQ ID NO:11) and amino acid(SEQ ID NO:12) sequence of human MSP (Gene Bank #L11924; Yoshimura, T., et al., 1993, J. Biol. Chem., 268:15461–15468). In contrast with the cited reference, in the numbering used herein nucleo-tide No. 1 is the first base of the initiation codon (the A of the first ATG). The first amino acid is methionine. The cDNA untranslated regions at 5' and 3' are not represented neither considered in the numbering.

FIG. 2:
a) Molecular structure of the factor Alphabet-1.
Domain [A] is the $HGF_\alpha$ chain, domain B is the natural cleavage site of HGF, domain C is the $MSP_\beta$ chain and domain D is a poly-histidine Tag sequence (GNSAVDHHHHHH)(SEQ ID NO:13).

b) Nucleotide(SEQ ID NO:5) and amino acid(SEQ ID NO:6) sequence of Factor Alphabet-1.
The initiation (ATG) and stop (TAG) codons are underlined.

FIG. 3:
a) Molecular structure of the Factor Alphabet-RTKR.
This construct differs from factor Alphabet-1 in that its domain β includes the natural cleavage site of HGF plus a furine protease cleavage site.

b) Nucleotide(SEQ ID NO:7) and amino acid(SEQ ID NO:8) sequence of Factor Alphabet-RTKR.

Figure 4A:
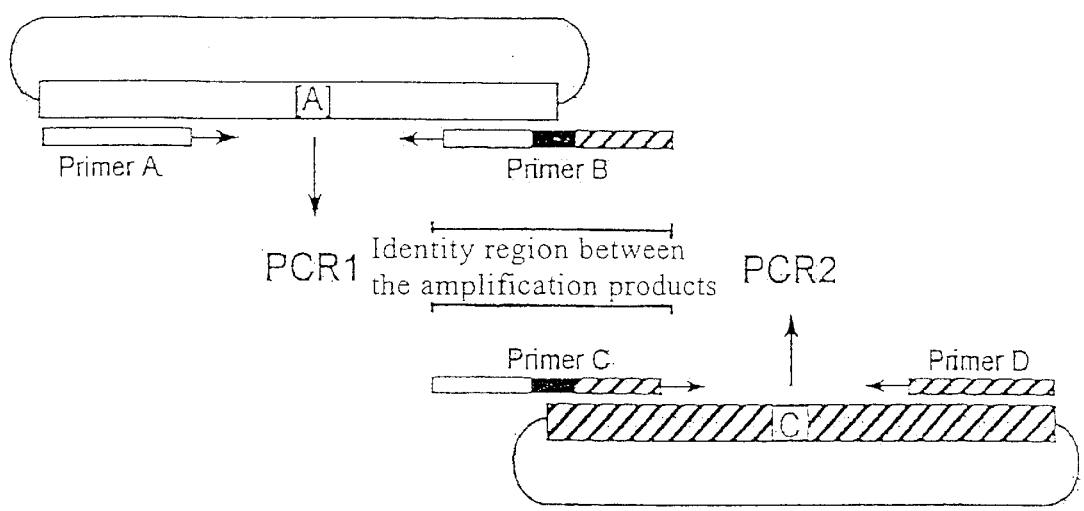
Figure 4B:
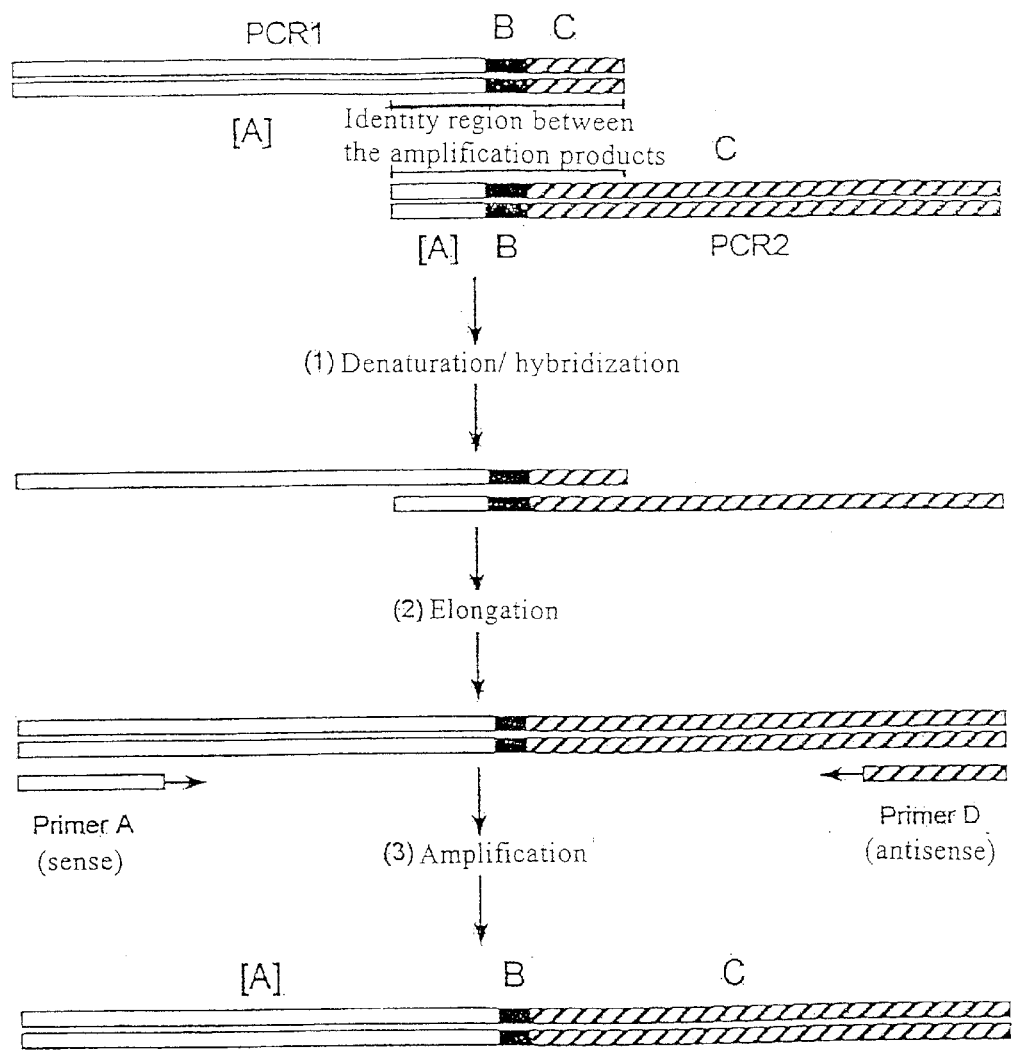

FIG. 4: production of the recombinant factors of the invention.
a) Amplification of domains A and C and their subsequent ligation.
The fragment named PCR1 is obtained by PCR from a plasmid containing a construct encoding domain A (α chain), whereas the one named PCR-2 is obtained by PCR from a plasmid containing a construct encoding domain C (β chain). Contained within both primers B and C is an identical sequence which encodes the potential proteolytic cleavage site (domain B, coloured in black). Being inserted in between the two amplification products, this sequence allows subsequent joining of the A and C domains.

b) Hybridisation of the fragments and amplification of the recombinant factor. The two amplificated PCR1 and PCR2 are mixed and subjected to the following treatments: (1) first denaturation at 95° C. for 3 min. and subsequent hybridisation for 30 sec.; (2) elongation at 72° C. for 9 min in the presence of a thermostable DNA polymerase. Steps (1) and (2) are repeated for a further four times only modifying the denaturation conditions, which are set at 94° C. for 30 sec.; (3) subsequently the mixture is added with primers A and D (already used for the first amplification of the constructs) and a conventional PCR is carried out to amplificate the recombinant construct.

Figure 5:
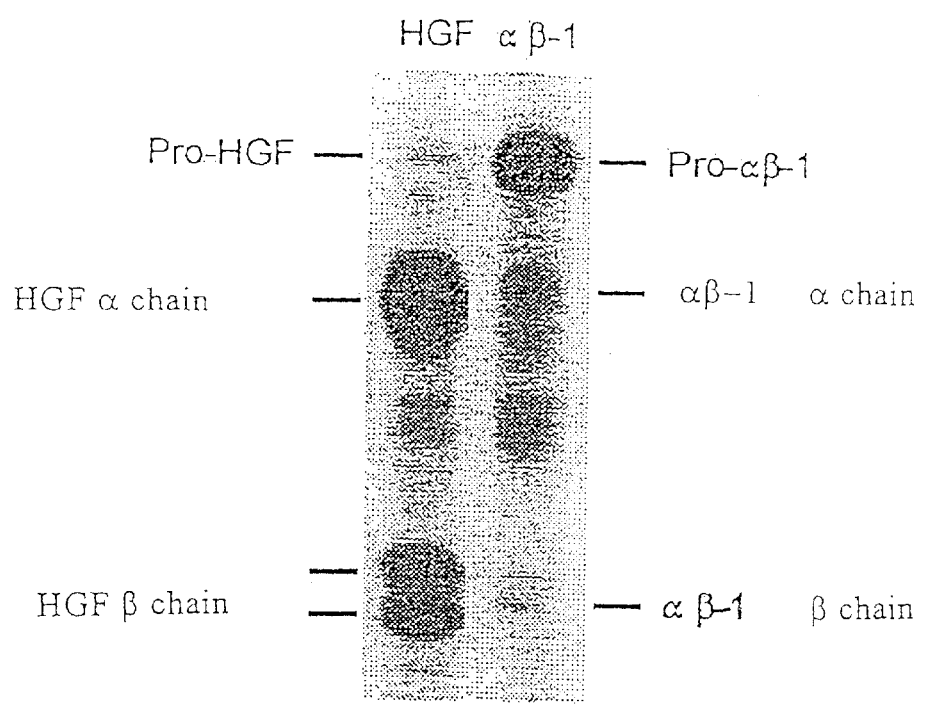

FIG. 5: Production of recombinant factor Alphabet-1.
The metabolically labelled proteins were absorbed on Sepharose-heparin beads and detected by autoradiography after electrophoresis on polyacrylamide gel. Immature forms of HGF (Pro-HGF, control) and Alphabet-1 (Pro-αβ-1), and α and β chains of HGF and Alphabet-1 are indicated.

Figure 6:
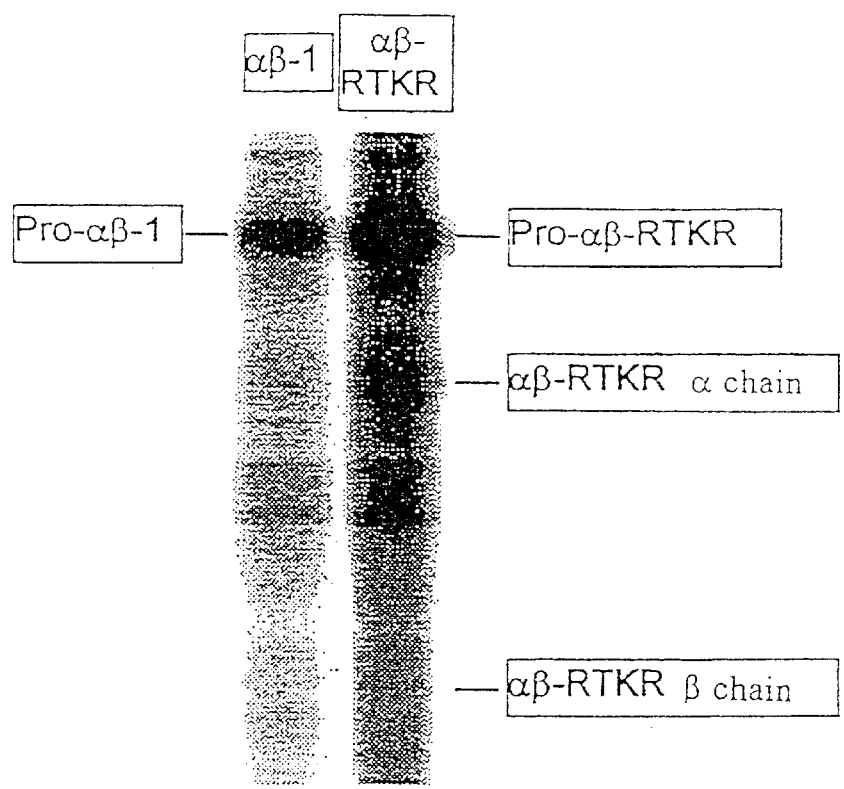

FIG. 6: Production of recombinant factor Alphabet-RTKR.
The metabolically labelled proteins were absorbed on Sepharose-heparin beads and detected by autoradiography after electrophoresis on polyacrylamide gel. Immature forms of Alphabet-1 (Pro-αβ-1) and Alphabet-RTKR (Pro-αβ-RTKR), and α and β chains of Alphabet-RTKR are indicated.

The examples reported in the following illustrate the invention in greater detail.

EXAMPLE 1

Preparation of the Recombinant Construct Encoding Factor Alphabet-1

HGF and MSP cDNAs shown in FIGS. 1 and 2 were used as starting DNA. HGF cDNA was obtained with the RT-PCR technique (Reverse Transcriptase PCR; in: Innis, M. A., et al., PCR Protocols, Academic Press, 1990, 21–27) human lung fibroblasts cell line (MRC5; Naldini, L. et al., 1991, EMBO J. 10: 2867–2878). MSP cDNA was obtained with the same technique from human liver (Gaudino, G., et al., 1994, EMBO J. 13: 3524–3532).

The fragment corresponding to $HGF_\alpha$ chain was amplificated by PCR from HGF cDNA, subcloned in the plasmid pBluescript SK (GenBank #52325) in the site EcoRV using the following primers:

Primer A (Sense)
5'        CCACCGCGGTGGCGGCCGC<u>TCTAGA</u>ACT-AGTGGATC 3'(SEQ ID NO:16)

Primer B (Antisense)
5' <u>gcccccaaccac</u>TCGCAATTGTTTCGTTTT 3'(SEQ ID NO:17)

In Primer A, which is derived from the plasmid-pBluescript sequence polycloning site, the underlined sequence is the restriction site for enzyme Xbal, upstream the site EcoRV from which HGF cDNA starts. The underlined sequence of Primer B is the region overlapping with Primer C (the lower-letter sequence corresponds to the first bases of $MSP_\alpha$ chain). The sequence of the cleavage site (TTGCGAGTGGTT)(SEQ ID NO:18) is generated by the identical regions of Primers B and C. The PCR product (PCR1) was then purified by electrophoresis on agarose gel.

The fragment corresponding to $MSP_\beta$ chain was amplificated by PCR from MSP cDNA using the following primers:
Primer C (Sense)

5' aaacaattgcgaGTGGTTGGGGGCCATCCG 3'(SEQ ID NO:19)

Primer D (Antisense)

5' CCCAAGCTTTCAAT GATGATGATGATGATGATGGTCGACGGCGCTATCCC acccagtctcatgaccttg 3'(SEQ ID NO:20)

The underlined sequence in Primer C is the region overlapping with Primer B (the small-letter sequence corresponds to the last bases of HGF α chain).

In Primer D, the sequence AAGCTT is the restriction site for enzyme HindIII, the tag-encoding sequence is underlined and the portion in small-letters corresponds to the last bases of MSP β chain. The PCR product (PCR2) was then purified by electrophoresis on agarose gel.

The two amplificates PCR1 and PCR2 were mixed and subjected to the following treatments: (1) first denaturation at 95° C. for 3 min and subsequent hybridisation at 68° C. (hybridisation temperature calculated on the basis of the identity region between Primers B and C) for 30 sec.; (2) elongation at 72° C. for 2 min. in the presence of a thermostable DNA polymerase. Steps (1) and (2) were repeated for a further four times modifying the conditions of denaturation, carried out at 92° C. for 1 min, and lowering hybridisation temperature by 1° C. at each cycle; (3) subsequently the mixture was added with primers A and D already used for the first amplification of the constructs and a conventional PCR was carried out to amplificate the recombinant construct.

The resulting PCR product was digested with the restriction enzymes XbaI and HindIII, purified by electrophoresis on agarose gel and subcloned in XbaI-HindIII sites of the expression vector pcDNA3.1(−) (Invitrogen), thereby obtaining a recombinant plasmid, containing the complete Alphabet-1 (in the following named pcDNA3-Alphabet-1).

EXAMPLE 2

Preparation of the Recombinant Construct Encoding Factor Alphabet-RTKR

Plasmid pCDNA3-Alphabet-1 described above was used as starting DNA. The cDNA of Alphabet-1 contains two restriction sites for the enzyme BglII, at position 1204 and 1744, respectively. Using these sites, the original sequence 1204–1744 (containing the cleavage site) was replaced by a cassette in which the sequence RTKR(SEQ ID NO:21) (consense for cleavage by furine proteases) is added by site-specific mutagenesis upstream the HGF cleavage natural site.

For this purpose, two amplificates from Alphabet-1 cDNA were prepared by PCR. The first (PCR3), corresponding to the fragment $BglII_{1204}$-"cleavage site" of Alphabet-1, was amplificated using the following primers:
Primer G (Sense)

5' ATCCCAAACAAGATCTGGACTAACATGTTC 3'(SEQ ID NO:22)

Primer H (Antisense)

5' CTCGCAATCGTTTCGTTCTGGCACAAGAT-ATTAC 3'(SEQ ID NO:23)

The underlined sequence in Primer G is the restriction site for enzyme BglII. In Primer H the bold-faced bases are point mutations inserted in the oligonucleotide to create the sequence RTKR(SEQ ID NO:21) upstream the HGF cleavage sequence, whereas the underlined sequence is the region identical with Primer 1. The PCR product (PCR3) was then purified by electrophoresis on agarose gel.

The second amplificate (PCR4), corresponding to the fragment "cleavage site"-$BglII_{1744}$ of Alphabet-1, was obtained using the following primers:
Primer I (Sense)

5' TCTTGTGCCAGAACGAAACGATTGCGAGTGG 3'(SEQ ID NO:24)

Primer L (Antisense)

5' GGTCACAGATCTCTCCAGCTTGAG 3'(SEQ ID NO:25)

In Primer I, bold-faced bases are point mutations inserted in the oligonucleotide to create sequence RTKR(SEQ ID NO:21), whereas the underlined sequence is the region of identity with Primer H. The underlined sequence in Primer L is the restriction site for enzyme BglII. The PCR product (PCR4) was then purified by electrophoresis on agarose gel.

The two amplificates PCR3 and PCR4 were mixed and subjected to the following treatments: (1) first denaturation at 95° C. for 3 min and subsequent hybridisation at 68° C. (hybridisation temperature calculated on the basis of the region of identity of Primers H and I) for 30 sec.; (2) elongation at 72° C. for 2 min. in the presence of a thermostable DNA polymerase. Steps (1) and (2) were repeated for a further four times modifying the conditions of denaturation, carried out at 92° C. for 1 min., and lowering by 1° C. the hybridisation temperature at each cycle; (3) subsequently the mixture was added with primers G and L already used for the first amplification of the constructs and a conventional PCR was carried out to amplificate the recombinant construct. The resulting PCR recombinant product was digested with the restriction enzyme BglII, purified by electrophoresis on agarose gel and subcloned in the plasmid pCDNA3-Alphabet-1 by replacing the fragment $BglII_{1204}$–$BglII_{1744}$ originally present.

EXAMPLE 3

Production of the Recombinant Molecules

The expression vector pcDNA3 contains the promoter of human cytomegalovirus immediate-early gene (CMV) and the episomal replication origin site of virus SV40. Therefore, this plasmid is particularly suitable for the expression of proteins in cells expressing the large T antigen of the virus SV40, such as kidney epithelial BOSC cells (Sambrook, J. et al., *Molecular Cloning*, Cold Spring Harbor Laboratory Press, 1989). The molecules Alphabet-1 and Alphabet-RTKR subcloned in pcDNA3 can be then produced by transient transfection in BOSC cells.

For transfection, $10^6$ cells per 100 mm diameter plate are seeded at day 0 in 90% Dulbecco's Modified Eagle Medium (DMEM)-10% bovine calf serum (10 ml/plate). At day 1, the cells are transfected with 10 μg/plate of pcDNA3-) Alphabet-1 (or pcDNA3-Alphabet-RTKR) by lipofection, according to the protocol provided by the lipofectin producer (Gibco-BRL). At day 2, the DNA-containing medium is replaced by fresh medium. At day 4 (48 hours after the end of the transfection), the medium is collected, cleared by centrifugation, and analysed for its content in Alphabet-1 or Alphabet-RTKR.

This analysis can be carried out in different ways. For example, the recombinant protein can be metabolically labelled incubating the transfected cells with medium containing $^{35}$S-Methionine (0.25 mCi/ml). The thus labelled protein can then be partially purified by adsorption on Sepharose-heparin beads and detected by autoradiography after electrophoresis on polyacrylamide gel (FIGS. 5 and 6).

In example shown in FIG. 5, $10^6$ BOSC cells transfected respectively with pcDNA3-HGF (control) and pcDNA3-Alphabet-1 were incubated at day 2 for 24 h in 4 ml of DMEM-Cys⁻-Met⁻ in the presence of 0.25 mCi/ml of $^{35}$SMet+Cys (Promix, Amersham) and 10% FCS (Sigma). 3.5 ml of supernatant (cleared by centrifugation, buffered in 25 mM HEPES and added with protease inhibitors cocktail) were incubated for 4 hours at 4° C. in the presence of 500 mM NaCl with 50 µL of Sepharose-heparin beads (Pierce). Then the beads were washed with suitable buffer (500 mM NaCl; 20 mM HEPES pH 7.4; 0.1% Triton X-100; 10% glycerol) and heated for 2 minutes at 90° C. in 50 µl of Laemmli buffer in the presence of 2-mercaptoethanol. The thus eluted proteins were separated by SDS-PAGE on a 10% polyacrylamide gel and analysed by autoradiography. As clearly seen in the figure, Alphabet-1 is mainly secreted as uncleaved precursor, notwithstanding the presence of foetal serum in high concentration (10%) in the medium.

In the example shown in FIG. 6, $10^6$ BOSC cells transfected respectively with pcDNA3-Alphabet-1 (control) and pcDNA3-Alphabet-RTKR were incubated from day 2 for 24 h in 4 ml of DMEM-Cys⁻-Met⁻ in the presence of 0.25 mCi/ml of $^{35}$SMet+Cys (Promix, Amersham) and 2% FCS (Sigma). 3.5 ml of supernatant (cleared by centrifugation, buffered in 25 mM HEPES and added with protease inhibitors cocktail) were incubated for 4 hours at 4° C. in the presence of 500 mM NaCl with 50 µl of Sepharose-heparin beads (Pierce). Then the beads were washed with suitable buffer (500 mM NaCl; 20 mM HEPES pH 7.4; 0.1% Triton X-100; 10% glycerol) and heated for 2 minutes at 90° C. in 50 µl of Laemmli buffer in the presence of 2-mercaptoethanol. The thus eluted proteins were separated by SDS-PAGE on a 10% polyacrylamide gel and analyzed by autoradiography. As evidenced in the figure, notwithstanding the low concentration of foetal serum (2%) in the medium, the Pro-Alphabet-RTKR precursor is cleaved to give the mature form, contrary to Alphabet-1 which is present only as precursor.

The adsorption procedure on Sepharose-heparin beads can be used also for the first purification of the recombinant protein. The molecule can be further purified using poly-histidine affinity to heavy metals such as nickel. The protein containing poly-histidine tag can be adsorbed on a nickel resin column (Invitrogen) and subsequently eluted with imidazole (the detailed protocol is provided by the manufacturer).

In the following sequence listing:

SEQ. ID. NO. 1: Alphabet-1 DNA coding sequence;
SEQ. ID. NO. 2: Alphabet-1 amino acid sequence;
SEQ. ID. NO. 3: Alphabet-RTKR DNA coding sequence;
SEQ. ID. NO. 4: Alphabet-RTKR amino acid sequence.

What is claimed is:

1. A recombinant protein of the formula:

wherein $LS_{HGF}$—$HL_{HGF}$—$K1_{HGF}$—$K2_{HGF}$—$K3_{HGF}$—$K4_{HGF}$ is the sequence comprising amino acids 1–487 of HGF (SEQ ID NO:27), $B_{HGF}$ is the sequence LLRVV (SEQ ID NO:26), $C\beta_{MSP}$ is the sequence 486–711 of MSP (SEQ ID NO:28), and D is the sequence $GNSAVD(H)_6$ (SEQ ID NO: 13).

2. A recombinant protein of formula:

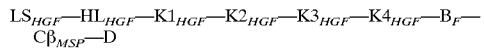

wherein $LS_{HGF}$—$HL_{HGF}$—$K1_{HGF}$—$K2_{HGF}$—$K3_{HGF}$—$K4_{HGF}$ is the sequence 1–487 of HGF SEQ ID NO:27), $B_F$ is the sequence RTKR-LRVV (SEQ ID NO: 15), $C\beta_{MSP}$ is the sequence 486–711 of MSP (SEQ ID NO:28), and D is the sequence $GNSAVD(H)_6$ (SEQ ID NO:13).

3. A method for the treatment of chemotherapeutic-induced toxicity which comprises administering to a patient who has or is to be exposed to chemotherapeutic-induced toxicity a pharmaceutical composition that contains an effective amount of the recombinant protein of claim 1 or claim 2, together with a pharmacologically acceptable expipient.

4. The method according to claim 3, wherein the chemotherapeutic-induced toxicity is myelotoxicity, hepatotoxicity, nefrotoxicity, mucotoxicity, or neurotoxicity.

5. A pharmaceutical composition containing an effective amount of the recombinant protein of claim 1 or claim 2, together with a pharmacologically acceptable excipient.

6. The method according to claim 4, wherein the chemotherapeutic-induced toxicity is apoptosis on differentiated cell elements of liver, kidney, and mucosa of the gastroenteral tract.

* * * * *

SEQUENCE LISTING

```
<160> NUMBER OF SEQ ID NOS: 28

<210> SEQ ID NO 1
<211> LENGTH: 2190
<212> TYPE: DNA
<213> ORGANISM: Artificial Sequence
<220> FEATURE:
<223> OTHER INFORMATION: Recombinant sequence derived from Homo sapiens

<400> SEQUENCE: 1
atgtgggtga ccaaactcct gccagccctg ctgctgcagc atgtcctcct gcatctcctc      60 ctgctccca tcgccatccc ctatgcagag ggacaaagga aagaagaaa tacaattcat       120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa aacaatgcct ctggttcccc     300
ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta agagtggcat caaatgtcag ccctggagtt ccatgatacc acacgaacac     480
agctatcggg gtaaagacct acaggaaaac tactgtcgaa atcctcgagg ggaagaaggg     540
ggaccctggt gtttcacaag caatccagag gtacgctacg aagtctgtga cattcctcag     600
tgttcagaag ttgaatgcat gacctgcaat ggggagagtt atcgaggtct catggatcat     660
acagaatcag gcaagatttg tcagcgctgg gatcatcaga caccacaccg gcacaaattc     720
ttgcctgaaa gatatcccga caagggcttt gatgataatt attgccgcaa tcccgatggc     780
cagccgaggc catggtgcta tactcttgac cctcacaccc gctgggagta ctgtgcaatt     840
```

-continued

```
aaaacatgcg ctgacaatac tatgaatgac actgatgttc ctttggaaac aactgaatgc    900
atccaaggtc aaggagaagg ctacagggc actgtcaata ccatttggaa tggaattcca     960
tgtcagcgtt gggattctca gtatcctcac gagcatgaca tgactcctga aatttcaag    1020
tgcaaggacc tacgagaaaa ttactgccga atccagatg ggtctgaatc accctggtgt    1080
tttaccactg atccaaacat ccgagttggc tactgctccc aaattccaaa ctgtgatatg    1140
tcacatggac aagattgtta tcgtgggaat ggcaaaaatt atatgggcaa cttatcccaa    1200
acaagatctg gactaacatg ttcaatgtgg gacaagaaca tggaagactt acatcgtcat    1260
atcttctggg aaccagatgc aagtaagctg aatgagaatt actgccgaaa tccagatgat    1320
gatgctcatg gaccctggtg ctacacggga atccactca ttccttggga ttattgccct    1380
atttctcgtt gtgaaggtga taccacacct acaatagtca atttagacca tcccgtaata    1440
tcttgtgcca aaacgaaaca attgcgagtg gttggggggcc atccgggcaa ctcaccctgg    1500
acagtcagct tgcggaatcg gcagggccag catttctgcg ggggtctct agtgaaggag    1560
cagtggatac tgactgcccg gcagtgcttc tcctcctgcc atatgcctct cacgggctat    1620
gaggtatggt tgggcaccct gttccagaac ccacagcatg gagagccaag cctacagcgg    1680
gtcccagtag ccaagatggt gtgtgggccc tcaggctccc agcttgtcct gctcaagctg    1740
gagagatctg tgaccctgaa ccagcgtgtg ccctgatct gcctgccccc tgaatggtat    1800
gtggtgcctc cagggaccaa gtgtgagatt gcaggctggg gtgagaccaa aggtacgggt    1860
aatgacacag tcctaaatgt ggcctttctg aatgttatct ccaaccagga gtgtaacatc    1920
aagcaccgag acgtgtgcg ggagagtgag atgtgcactg agggactgtt ggccctgtg    1980
ggggcctgtg agggtgacta cggggccca cttgcctgct ttacccacaa ctgctgggtc    2040
ctggaaggaa ttataatccc caaccgagta tgcgcaaggt cccgctggcc agctgtcttc    2100
acgcgtgtct ctgtgtttgt ggactggatt cacaaggtca tgagactggg tgggaatagc    2160
gccgtcgacc atcatcatca tcatcattga                                     2190
```

<210> SEQ ID NO 2
<211> LENGTH: 729
<212> TYPE: PRT
<213> ORGANISM: Artificial Sequence
<220> FEATURE:
<223> OTHER INFORMATION: Recombinant sequence derived from Homo sapiens

<400> SEQUENCE: 2

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125
```

-continued

```
Ile Ile Gly Lys Gly Arg Ser Tyr Lys Gly Thr Val Ser Ile Thr Lys
    130                 135                 140
Ser Gly Ile Lys Cys Gln Pro Trp Ser Ser Met Ile Pro His Glu His
145                 150                 155                 160
Ser Tyr Arg Gly Lys Asp Leu Gln Glu Asn Tyr Cys Arg Asn Pro Arg
                165                 170                 175
Gly Glu Glu Gly Gly Pro Trp Cys Phe Thr Ser Asn Pro Glu Val Arg
            180                 185                 190
Tyr Glu Val Cys Asp Ile Pro Gln Cys Ser Glu Val Glu Cys Met Thr
        195                 200                 205
Cys Asn Gly Glu Ser Tyr Arg Gly Leu Met Asp His Thr Glu Ser Gly
    210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
            260                 265                 270
Thr Arg Trp Glu Tyr Cys Ala Ile Lys Thr Cys Ala Asp Asn Thr Met
        275                 280                 285
Asn Asp Thr Asp Val Pro Leu Glu Thr Thr Glu Cys Ile Gln Gly Gln
    290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
    370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Asp Ala His Gly Pro Trp Cys Tyr
        435                 440                 445
Thr Gly Asn Pro Leu Ile Pro Trp Asp Tyr Cys Pro Ile Ser Arg Cys
    450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Gly His Pro Gly
                485                 490                 495
Asn Ser Pro Trp Thr Val Ser Leu Arg Asn Arg Gln Gly Gln His Phe
            500                 505                 510
Cys Gly Gly Ser Leu Val Lys Glu Gln Trp Ile Leu Thr Ala Arg Gln
        515                 520                 525
Cys Phe Ser Ser Cys His Met Pro Leu Thr Gly Tyr Glu Val Trp Leu
    530                 535                 540
```

-continued

Gly Thr Leu Phe Gln Asn Pro Gln His Gly Glu Pro Ser Leu Gln Arg
545                 550                 555                 560

Val Pro Val Ala Lys Met Val Cys Gly Pro Gly Ser Gln Leu Val
                565                 570                 575

Leu Leu Lys Leu Glu Arg Ser Val Thr Leu Asn Gln Arg Val Ala Leu
                580                 585                 590

Ile Cys Leu Pro Pro Glu Trp Tyr Val Val Pro Pro Gly Thr Lys Cys
                595                 600                 605

Glu Ile Ala Gly Trp Gly Glu Thr Lys Gly Thr Gly Asn Asp Thr Val
                610                 615                 620

Leu Asn Val Ala Phe Leu Asn Val Ile Ser Asn Gln Glu Cys Asn Ile
625                 630                 635                 640

Lys His Arg Gly Arg Val Arg Glu Ser Glu Met Cys Thr Glu Gly Leu
                645                 650                 655

Leu Ala Pro Val Gly Ala Cys Glu Gly Asp Tyr Gly Gly Pro Leu Ala
                660                 665                 670

Cys Phe Thr His Asn Cys Trp Val Leu Glu Gly Ile Ile Ile Pro Asn
                675                 680                 685

Arg Val Cys Ala Arg Ser Arg Trp Pro Ala Val Phe Thr Arg Val Ser
                690                 695                 700

Val Phe Val Asp Trp Ile His Lys Val Met Arg Leu Gly Gly Asn Ser
705                 710                 715                 720

Ala Val Asp His His His His His His
                725

<210> SEQ ID NO 3
<211> LENGTH: 2190
<212> TYPE: DNA
<213> ORGANISM: Artificial Sequence
<220> FEATURE:
<223> OTHER INFORMATION: Recombinant sequence derived from Homo sapiens

<400> SEQUENCE: 3
atgtgggtga ccaaactcct gccagccctg ctgctgcagc atgtcctcct gcatctcctc         60
ctgctcccca tcgccatccc ctatgcagag ggacaaagga aagaagaaa tacaattcat        120 gaattcaaaa aatcagcaaa gactaccta atcaaaatag atccagcact gaagataaaa        180
accaaaaaag tgaatactgc agaccaatgt gctaatagat gtactaggaa taaggactt         240 ccattcactt gcaaggcttt tgtttttgat aaagcaagaa acaatgcct ctggttcccc         300 ttcaatagca tgtcaagtgg agtgaaaaaa gaatttggcc atgaatttga cctctatgaa        360
aacaaagact acattagaaa ctgcatcatt ggtaaaggac gcagctacaa gggaacagta        420
tctatcacta agagtggcat caaatgtcag ccctggagtt ccatgatacc acacgaacac        480
agctatcggg gtaaagacct acaggaaaac tactgtcgaa atcctcgagg ggaagaaggg        540
ggaccctggt gtttcacaag caatccagag gtacgctacg aagtctgtga cattcctcag        600
tgttcagaag ttgaatgcat gacctgcaat ggggagagtt atcgaggtct catggatcat        660
acagaatcag gcaagatttg tcagcgctgg gatcatcaga caccacaccg gcacaaattc        720
ttgcctgaaa gatatcccga caagggcttt gatgataatt attgccgcaa tcccgatggc        780
cagccgaggc catggtgcta tactcttgac cctcacaccc gctgggagta ctgtgcaatt        840
aaaacatgcg ctgacaatac tatgaatgac actgatgttc ctttggaaac aactgaatgc        900
atccaaggtc aaggagaagg ctacaggggc actgtcaata ccatttggaa tggaattcca        960
tgtcagcgtt gggattctca gtatcctcac gagcatgaca tgactcctga aaatttcaag       1020

```
tgcaaggacc tacgagaaaa ttactgccga atccagatg ggtctgaatc accctggtgt    1080
tttaccactg atccaaacat ccgagttggc tactgctccc aaattccaaa ctgtgatatg    1140
tcacatggac aagattgtta tcgtgggaat ggcaaaaatt atatgggcaa cttatcccaa    1200
acaagatctg gactaacatg ttcaatgtgg acaagaaca tggaagactt acatcgtcat    1260
atcttctggg aaccagatgc aagtaagctg aatgagaatt actgccgaaa tccagatgat    1320
gacgctcatg gaccctggtg ctacacggga atccactca ttccttggga ttattgccct    1380
atttctcgtt gtgaaggtga taccacacct acaatagtca atttagacca tcccgtaata    1440
tcttgtgcca gaacgaaacg attgcgagtg gttggggggcc atccgggcaa ctcaccctgg    1500
acagtcagct tgcggaatcg gcagggccag catttctgcg gggggtctct agtgaaggag    1560
cagtggatac tgactgcccg gcagtgcttc tcctcctgcc atatgcctct cacgggctat    1620
gaggtatggt tgggcaccct gttccagaac ccacagcatg agagccaag cctacagcgg    1680 gtcccagtag ccaagatggt gtgtgggccc tcaggctccc agcttgtcct gctcaagctg    1740
gagagatctg tgaccctgaa ccagcgtgtg gccctgatct gcctgccccc tgaatggtat    1800
gtggtgcctc cagggaccaa gtgtgagatt gcaggctggg gtgagaccaa aggtacgggt    1860
aatgacacag tcctaaatgt ggccttgctg aatgtcatct ccaaccagga gtgtaacatc    1920
aagcaccgag gacgtgtgcg ggagagtgag atgtgcactg agggactgtt ggcccctgtg    1980
ggggcctgtg agggtgacta cgggggccca cttgcctgct ttaccacaa ctgctgggtc    2040 ctggaaggaa ttataatccc caaccgagta tgcgcaaggt cccgctggcc agctgtcttc    2100
acgcgtgtct ctgtgtttgt ggactggatt cacaaggtca tgagactggg tgggaatagc    2160
gccgtcgacc atcatcatca tcatcattga                                    2190
```

<210> SEQ ID NO 4
<211> LENGTH: 729
<212> TYPE: PRT
<213> ORGANISM: Artificial Sequence
<220> FEATURE:
<223> OTHER INFORMATION: Recombinant sequence derived from Homo sapiens

<400> SEQUENCE: 4

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
```

```
145                 150                 155                 160
Ser Tyr Arg Gly Lys Asp Leu Gln Glu Asn Tyr Cys Arg Asn Pro Arg
                165                 170                 175
Gly Glu Glu Gly Gly Pro Trp Cys Phe Thr Ser Asn Pro Glu Val Arg
                180                 185                 190
Tyr Glu Val Cys Asp Ile Pro Gln Cys Ser Glu Val Glu Cys Met Thr
                195                 200                 205
Cys Asn Gly Glu Ser Tyr Arg Gly Leu Met Asp His Thr Glu Ser Gly
                210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
                260                 265                 270
Thr Arg Trp Glu Tyr Cys Ala Ile Lys Thr Cys Ala Asp Asn Thr Met
                275                 280                 285
Asn Asp Thr Asp Val Pro Leu Glu Thr Thr Glu Cys Ile Gln Gly Gln
                290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
                340                 345                 350
Asp Gly Ser Glu Ser Pro Trp Cys Phe Thr Thr Asp Pro Asn Ile Arg
                355                 360                 365
Val Gly Tyr Cys Ser Gln Ile Pro Asn Cys Asp Met Ser His Gly Gln
                370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
                420                 425                 430
Asn Tyr Cys Arg Asn Pro Asp Asp Ala His Gly Pro Trp Cys Tyr
                435                 440                 445
Thr Gly Asn Pro Leu Ile Pro Trp Asp Tyr Cys Pro Ile Ser Arg Cys
                450                 455                 460
Glu Gly Asp Thr Thr Pro Thr Ile Val Asn Leu Asp His Pro Val Ile
465                 470                 475                 480
Ser Cys Ala Arg Thr Lys Arg Leu Arg Val Val Gly His Pro Gly
                485                 490                 495
Asn Ser Pro Trp Thr Val Ser Leu Arg Asn Arg Gln Gly Gln His Phe
                500                 505                 510
Cys Gly Gly Ser Leu Val Lys Glu Gln Trp Ile Leu Thr Ala Arg Gln
                515                 520                 525
Cys Phe Ser Ser Cys His Met Pro Leu Thr Gly Tyr Glu Val Trp Leu
                530                 535                 540
Gly Thr Leu Phe Gln Asn Pro Gln His Gly Glu Pro Ser Leu Gln Arg
545                 550                 555                 560
Val Pro Val Ala Lys Met Val Cys Gly Pro Ser Gly Ser Gln Leu Val
                565                 570                 575
```

```
Leu Leu Lys Leu Glu Arg Ser Val Thr Leu Asn Gln Arg Val Ala Leu
            580                 585                 590

Ile Cys Leu Pro Pro Glu Trp Tyr Val Val Pro Pro Gly Thr Lys Cys
        595                 600                 605

Glu Ile Ala Gly Trp Gly Glu Thr Lys Gly Thr Gly Asn Asp Thr Val
        610                 615                 620

Leu Asn Val Ala Leu Leu Asn Val Ile Ser Asn Gln Glu Cys Asn Ile
625                 630                 635                 640

Lys His Arg Gly Arg Val Arg Glu Ser Glu Met Cys Thr Glu Gly Leu
                645                 650                 655

Leu Ala Pro Val Gly Ala Cys Glu Gly Asp Tyr Gly Gly Pro Leu Ala
            660                 665                 670

Cys Phe Thr His Asn Cys Trp Val Leu Glu Gly Ile Ile Ile Pro Asn
        675                 680                 685

Arg Val Cys Ala Arg Ser Arg Trp Pro Ala Val Phe Thr Arg Val Ser
        690                 695                 700

Val Phe Val Asp Trp Ile His Lys Val Met Arg Leu Gly Gly Asn Ser
705                 710                 715                 720

Ala Val Asp His His His His His His
                725

<210> SEQ ID NO 5
<211> LENGTH: 2154
<212> TYPE: DNA
<213> ORGANISM: Artificial Sequence
<220> FEATURE:
<223> OTHER INFORMATION: Recombinant sequence derived from Homo sapiens

<400> SEQUENCE: 5
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa atcagcaaa gactaccctaa atcaaaatag atccagcact gaagataaaa     180
accaaaaaag tgaatactgc agaccaatgt gctaatagat gtactaggaa taaggactt      240 ccattcactt gcaaggcttt tgtttttgat aaagcaagaa aacaatgcct ctggttcccc    300
ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta agagtggcat caaatgtcag ccctggagtt ccatgatacc acacgaacac    480
agctatcggg gtaaagacct acaggaaaac tactgtcgaa atcctcgagg ggaagaaggg    540
ggaccctggt gtttcacaag caatccagag gtacgctacg aagtctgtga cattcctcag    600
tgttcagaag ttgaatgcat gacctgcaat ggggagagtt atcgaggtct catggatcat    660
acagaatcag gcaagatttg tcagcgctgg gatcatcaga caccacaccg gcacaaattc    720
ttgcctgaaa gatatcccga caagggcttt gatgataatt attgccgcaa tcccgatggc    780
cagccgaggc catggtgcta tactcttgac cctcacaccc gctgggagta ctgtgcaatt    840
aaaacatgcg ctgacaatac tatgaatgac actgatgttc ctttggaaac aactgaatgc    900
atccaaggtc aaggagaagg ctacaggggc actgtcaata ccatttggaa tggaattcca    960
tgtcagcgtt gggattctca gtatcctcac gagcatgaca tgactcctga aaatttcaag   1020
tgcaaggacc tacgagaaaa ttactgccga atccagatgg gtctgaatc accctggtgt   1080 tttaccactg atccaaacat ccgagttggc tactgctccc aaattccaaa ctgtgatatg   1140
```

```
tcacatggac aagattgtta tcgtgggaat ggcaaaaatt atatgggcaa cttatcccaa    1200
acaagatctg gactaacatg ttcaatgtgg gacaagaaca tggaagactt acatcgtcat    1260
atcttctggg aaccagatgc aagtaagctg aatgagaatt actgccgaaa tccagatgat    1320
gatgctcatg gaccctggtg ctacacggga atccactca ttccttggga ttattgccct    1380
atttctcgtt gtgaaggtga taccacacct acaatagtca atttagacca tcccgtaata    1440
tcttgtgcca aaacgaaaca attgcgagtg gttgggggcc atccgggcaa ctcaccctgg    1500
acagtcagct tgcggaatcg gcagggccag catttctgcg gggggtctct agtgaaggag    1560
cagtggatac tgactgcccg gcagtgcttc tcctcctgcc atatgcctct cacgggctat    1620
gaggtatggt tgggcaccct gttccagaac ccacagcatg gagagccaag cctacagcgg    1680
gtcccagtag ccaagatggt gtgtgggccc tcaggctccc agcttgtcct gctcaagctg    1740
gagagatctg tgaccctgaa ccagcgtgtg ccctgatct gcctgccccc tgaatggtat    1800
gtggtgcctc cagggaccaa gtgtgagatt gcaggctggg gtgagaccaa aggtacgggt    1860
aatgacacag tcctaaatgt ggcctttctg aatgttatct ccaaccagga gtgtaacatc    1920
aagcaccgag gacgtgtgcg ggagagtgag atgtgcactg agggactgtt ggcccctgtg    1980 gggcctgtg aggtgactac cgggggccca cttgcctgct ttaccacaa ctgctgggtc    2040 ctggaaggaa ttataatccc caaccgagta tgcgcaaggt cccgctggcc agctgtcttc    2100
acgcgtgtct ctgtgtttgt ggactggatt cacaaggtca tgagactggg ttag          2154

<210> SEQ ID NO 6
<211> LENGTH: 717
<212> TYPE: PRT
<213> ORGANISM: Artificial Sequence
<220> FEATURE:
<223> OTHER INFORMATION: Recombinant sequence derived from Homo sapiens

<400> SEQUENCE: 6

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190
```

-continued

```
Tyr Glu Val Cys Asp Ile Pro Gln Cys Ser Glu Val Glu Cys Met Thr
                195                 200                 205
Cys Asn Gly Glu Ser Tyr Arg Gly Leu Met Asp His Thr Glu Ser Gly
            210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
            260                 265                 270
Thr Arg Trp Glu Tyr Cys Ala Ile Lys Thr Cys Ala Asp Asn Thr Met
            275                 280                 285
Asn Asp Thr Asp Val Pro Leu Glu Thr Thr Glu Cys Ile Gln Gly Gln
            290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
            355                 360                 365
Val Gly Tyr Cys Ser Gln Ile Pro Asn Cys Asp Met Ser His Gly Gln
            370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Asp Ala His Gly Pro Trp Cys Tyr
            435                 440                 445
Thr Gly Asn Pro Leu Ile Pro Trp Asp Tyr Cys Pro Ile Ser Arg Cys
450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Gly Gly His Pro Gly
                485                 490                 495
Asn Ser Pro Trp Thr Val Ser Leu Arg Asn Arg Gln Gly Gln His Phe
            500                 505                 510
Cys Gly Gly Ser Leu Val Lys Glu Gln Trp Ile Leu Thr Ala Arg Gln
            515                 520                 525
Cys Phe Ser Ser Cys His Met Pro Leu Thr Gly Tyr Glu Val Trp Leu
            530                 535                 540
Gly Thr Leu Phe Gln Asn Pro Gln His Gly Glu Pro Ser Leu Gln Arg
545                 550                 555                 560
Val Pro Val Ala Lys Met Val Cys Gly Pro Ser Gly Ser Gln Leu Val
                565                 570                 575
Leu Leu Lys Leu Glu Arg Ser Val Thr Leu Asn Gln Arg Val Ala Leu
            580                 585                 590
Ile Cys Leu Pro Pro Glu Trp Tyr Val Val Pro Pro Gly Thr Lys Cys
            595                 600                 605
```

```
Glu Ile Ala Gly Trp Gly Glu Thr Lys Gly Thr Gly Asn Asp Thr Val
        610                 615                 620

Leu Asn Val Ala Phe Leu Asn Val Ile Ser Asn Gln Glu Cys Asn Ile
625                 630                 635                 640

Lys His Arg Gly Arg Val Arg Glu Ser Glu Met Cys Thr Glu Gly Leu
                645                 650                 655

Leu Ala Pro Val Gly Ala Cys Glu Gly Asp Tyr Gly Gly Pro Leu Ala
            660                 665                 670

Cys Phe Thr His Asn Cys Trp Val Leu Glu Gly Ile Ile Ile Pro Asn
        675                 680                 685

Arg Val Cys Ala Arg Ser Arg Trp Pro Ala Val Phe Thr Arg Val Ser
690                 695                 700

Val Phe Val Asp Trp Ile His Lys Val Met Arg Leu Gly
705                 710                 715
```

<210> SEQ ID NO 7
<211> LENGTH: 2154
<212> TYPE: DNA
<213> ORGANISM: Artificial Sequence
<220> FEATURE:
<223> OTHER INFORMATION: Recombinant sequence derived from Homo sapiens

<400> SEQUENCE: 7

```
atgtgggtga ccaaactcct gccagccctg ctgctgcagc atgtcctcct gcatctcctc      60
ctgctcccca tcgccatccc ctatgcagag ggacaaagga aagaagaaa tacaattcat     120
gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa acaatgcct ctggttcccc      300
ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta agagtggcat caaatgtcag ccctggagtt ccatgatacc acacgaacac     480
agctatcggg gtaaagacct acaggaaaac tactgtcgaa atcctcgagg ggaagaaggg     540
ggaccctggt gtttcacaag caatccagag gtacgctacg aagtctgtga cattcctcag     600
tgttcagaag ttgaatgcat gacctgcaat ggggagagtt atcgaggtct catggatcat     660
acagaatcag gcaagatttg tcagcgctgg gatcatcaga caccacaccg gcacaaattc     720
ttgcctgaaa gatatcccga caagggcttt gatgataatt attgccgcaa tcccgatggc     780
cagccgaggc catggtgcta tactcttgac cctcacaccc gctgggagta ctgtgcaatt     840
aaaacatgcg ctgacaatac tatgaatgac actgatgttc ctttgaaac aactgaatgc     900
atccaaggtc aaggagaagg ctacaggggc actgtcaata ccatttggaa tggaattcca     960
tgtcagcgtt gggattctca gtatcctcac gagcatgaca tgactcctga aaatttcaag    1020
tgcaaggacc tacgagaaaa ttactgccga aatccagatg ggtctgaatc accctggtgt    1080
tttaccactg atccaaacat ccgagttggc tactgctccc aaattccaaa ctgtgatatg    1140
tcacatggac aagattgtta tcgtgggaat ggcaaaaatt atatgggcaa cttatcccaa    1200
acaagatctg gactaaacatg ttcaatgtgg gacaagaaca tggaagactt acatcgtcat    1260
atcttctggg aaccagatgc aagtaagctg aatgagaatt actgccgaaa tccagatgat    1320
gacgctcatg gacctggtg ctacacggga atccactca ttccttggga ttattgccct     1380
atttctcgtt gtgaaggtga taccacacct acaatagtca atttagacca tcccgtaata    1440
```

-continued

```
tcttgtgcca gaacgaaacg attgcgagtg gttgggggcc atccgggcaa ctcaccctgg    1500
acagtcagct tgcggaatcg gcagggccag catttctgcg gggggtctct agtgaaggag    1560
cagtggatac tgactgcccg gcagtgcttc tcctcctgcc atatgcctct cacgggctat    1620
gaggtatggt tgggcaccct gttccagaac ccacagcatg agagccaag cctacagcgg     1680 gtcccagtag ccaagatggt gtgtgggccc tcaggctccc agcttgtcct gctcaagctg    1740
gagagatctg tgaccctgaa ccagcgtgtg gccctgatct gcctgccccc tgaatggtat    1800
gtggtgcctc cagggaccaa gtgtgagatt gcaggctggg gtgagaccaa aggtacgggt    1860
aatgacacag tcctaaatgt ggccttgctg aatgtcatct ccaaccagga gtgtaacatc    1920
aagcaccgag gacgtgtgcg ggagagtgag atgtgcactg agggactgtt ggccctgtg     1980 ggggcctgtg aggtgactac cggggcccca cttgcctgct ttacccacaa ctgctgggtc    2040
ctggaaggaa ttataatccc caaccgagta tgcgcaaggt cccgctggcc agctgtcttc    2100
acgcgtgtct ctgtgtttgt ggactggatt cacaaggtca tgagactggg ttag          2154
```

<210> SEQ ID NO 8
<211> LENGTH: 717
<212> TYPE: PRT
<213> ORGANISM: Artificial Sequence
<220> FEATURE:
<223> OTHER INFORMATION: Recombinant sequence derived from Homo sapiens

<400> SEQUENCE: 8

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240
```

-continued

```
Leu Pro Glu Arg Tyr Pro Asp Lys Gly Phe Asp Asp Asn Tyr Cys Arg
            245                 250                 255
Asn Pro Asp Gly Gln Pro Arg Pro Trp Cys Tyr Thr Leu Asp Pro His
        260                 265                 270
Thr Arg Trp Glu Tyr Cys Ala Ile Lys Thr Cys Ala Asp Asn Thr Met
    275                 280                 285
Asn Asp Thr Asp Val Pro Leu Glu Thr Thr Glu Cys Ile Gln Gly Gln
290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
    370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Ala His Gly Pro Trp Cys Tyr
        435                 440                 445
Thr Gly Asn Pro Leu Ile Pro Trp Asp Tyr Cys Pro Ile Ser Arg Cys
    450                 455                 460
Glu Gly Asp Thr Thr Pro Thr Ile Val Asn Leu Asp His Pro Val Ile
465                 470                 475                 480
Ser Cys Ala Arg Thr Lys Arg Leu Arg Val Val Gly His Pro Gly
                485                 490                 495
Asn Ser Pro Trp Thr Val Ser Leu Arg Asn Arg Gln Gly Gln His Phe
            500                 505                 510
Cys Gly Gly Ser Leu Val Lys Glu Gln Trp Ile Leu Thr Ala Arg Gln
        515                 520                 525
Cys Phe Ser Ser Cys His Met Pro Leu Thr Gly Tyr Glu Val Trp Leu
    530                 535                 540
Gly Thr Leu Phe Gln Asn Pro Gln His Gly Glu Pro Ser Leu Gln Arg
545                 550                 555                 560
Val Pro Val Ala Lys Met Val Cys Gly Pro Ser Gly Ser Gln Leu Val
                565                 570                 575
Leu Leu Lys Leu Glu Arg Ser Val Thr Leu Asn Gln Arg Val Ala Leu
            580                 585                 590
Ile Cys Leu Pro Pro Glu Trp Tyr Val Val Pro Pro Gly Thr Lys Cys
        595                 600                 605
Glu Ile Ala Gly Trp Gly Glu Thr Lys Gly Thr Gly Asn Asp Thr Val
    610                 615                 620
Leu Asn Val Ala Leu Leu Asn Val Ile Ser Asn Gln Glu Cys Asn Ile
625                 630                 635                 640
Lys His Arg Gly Arg Val Arg Glu Ser Glu Met Cys Thr Glu Gly Leu
                645                 650                 655
Leu Ala Pro Val Gly Ala Cys Glu Gly Asp Tyr Gly Gly Pro Leu Ala
```

-continued

| | | | | | 660 | | | | 665 | | | | 670 | | |
|---|---|---|---|---|---|---|---|---|---|---|---|---|---|---|---|
| Cys | Phe | Thr | His | Asn | Cys | Trp | Val | Leu | Glu | Gly | Ile | Ile | Ile | Pro | Asn |
| | | | 675 | | | | | 680 | | | | | 685 | | |

| Arg | Val | Cys | Ala | Arg | Ser | Arg | Trp | Pro | Ala | Val | Phe | Thr | Arg | Val | Ser |
|---|---|---|---|---|---|---|---|---|---|---|---|---|---|---|---|
| | | 690 | | | | | 695 | | | | | 700 | | | |

| Val | Phe | Val | Asp | Trp | Ile | His | Lys | Val | Met | Arg | Leu | Gly |
|---|---|---|---|---|---|---|---|---|---|---|---|---|
| 705 | | | | | 710 | | | | | 715 | | |

<210> SEQ ID NO 9
<211> LENGTH: 2172
<212> TYPE: DNA
<213> ORGANISM: Homo sapiens
<220> FEATURE:
<221> NAME/KEY: CDS
<222> LOCATION: (1)..(2172)

<400> SEQUENCE: 9

| atg | tgg | gtg | acc | aaa | ctc | ctg | cca | gcc | ctg | ctg | ctg | cag | cat | gtc | ctc | 48 |
|---|---|---|---|---|---|---|---|---|---|---|---|---|---|---|---|---|
| Met | Trp | Val | Thr | Lys | Leu | Leu | Pro | Ala | Leu | Leu | Leu | Gln | His | Val | Leu | |
| 1 | | | | 5 | | | | | 10 | | | | | 15 | | |

| ctg | cat | ctc | ctc | ctg | ctc | ccc | atc | gcc | atc | ccc | tat | gca | gag | gga | caa | 96 |
|---|---|---|---|---|---|---|---|---|---|---|---|---|---|---|---|---|
| Leu | His | Leu | Leu | Leu | Leu | Pro | Ile | Ala | Ile | Pro | Tyr | Ala | Glu | Gly | Gln | |
| | | | 20 | | | | | 25 | | | | | 30 | | | |

| agg | aaa | aga | aga | aat | aca | att | cat | gaa | ttc | aaa | aaa | tca | gca | aag | act | 144 |
|---|---|---|---|---|---|---|---|---|---|---|---|---|---|---|---|---|
| Arg | Lys | Arg | Arg | Asn | Thr | Ile | His | Glu | Phe | Lys | Lys | Ser | Ala | Lys | Thr | |
| | | 35 | | | | | 40 | | | | | 45 | | | | |

| acc | cta | atc | aaa | ata | gat | cca | gca | ctg | aag | ata | aaa | acc | aaa | aaa | gtg | 192 |
|---|---|---|---|---|---|---|---|---|---|---|---|---|---|---|---|---|
| Thr | Leu | Ile | Lys | Ile | Asp | Pro | Ala | Leu | Lys | Ile | Lys | Thr | Lys | Lys | Val | |
| | 50 | | | | | 55 | | | | | 60 | | | | | |

| aat | act | gca | gac | caa | tgt | gct | aat | aga | tgt | act | agg | aat | aaa | gga | ctt | 240 |
|---|---|---|---|---|---|---|---|---|---|---|---|---|---|---|---|---|
| Asn | Thr | Ala | Asp | Gln | Cys | Ala | Asn | Arg | Cys | Thr | Arg | Asn | Lys | Gly | Leu | |
| 65 | | | | | 70 | | | | | 75 | | | | | 80 | |

| cca | ttc | act | tgc | aag | gct | ttt | gtt | ttt | gat | aaa | gca | aga | aaa | caa | tgc | 288 |
|---|---|---|---|---|---|---|---|---|---|---|---|---|---|---|---|---|
| Pro | Phe | Thr | Cys | Lys | Ala | Phe | Val | Phe | Asp | Lys | Ala | Arg | Lys | Gln | Cys | |
| | | | | 85 | | | | | 90 | | | | | 95 | | |

| ctc | tgg | ttc | ccc | ttc | aat | agc | atg | tca | agt | gga | gtg | aaa | aaa | gaa | ttt | 336 |
|---|---|---|---|---|---|---|---|---|---|---|---|---|---|---|---|---|
| Leu | Trp | Phe | Pro | Phe | Asn | Ser | Met | Ser | Ser | Gly | Val | Lys | Lys | Glu | Phe | |
| | | | 100 | | | | | 105 | | | | | 110 | | | |

| ggc | cat | gaa | ttt | gac | ctc | tat | gaa | aac | aaa | gac | tac | att | aga | aac | tgc | 384 |
|---|---|---|---|---|---|---|---|---|---|---|---|---|---|---|---|---|
| Gly | His | Glu | Phe | Asp | Leu | Tyr | Glu | Asn | Lys | Asp | Tyr | Ile | Arg | Asn | Cys | |
| | | 115 | | | | | 120 | | | | | 125 | | | | |

| atc | att | ggt | aaa | gga | cgc | agc | tac | aag | gga | aca | gta | tct | atc | act | aag | 432 |
|---|---|---|---|---|---|---|---|---|---|---|---|---|---|---|---|---|
| Ile | Ile | Gly | Lys | Gly | Arg | Ser | Tyr | Lys | Gly | Thr | Val | Ser | Ile | Thr | Lys | |
| | 130 | | | | | 135 | | | | | 140 | | | | | |

| agt | ggc | atc | aaa | tgt | cag | ccc | tgg | agt | tcc | atg | ata | cca | cac | gaa | cac | 480 |
|---|---|---|---|---|---|---|---|---|---|---|---|---|---|---|---|---|
| Ser | Gly | Ile | Lys | Cys | Gln | Pro | Trp | Ser | Ser | Met | Ile | Pro | His | Glu | His | |
| 145 | | | | | 150 | | | | | 155 | | | | | 160 | |

| agc | tat | cgg | ggt | aaa | gac | cta | cag | gaa | aac | tac | tgt | cga | aat | cct | cga | 528 |
|---|---|---|---|---|---|---|---|---|---|---|---|---|---|---|---|---|
| Ser | Tyr | Arg | Gly | Lys | Asp | Leu | Gln | Glu | Asn | Tyr | Cys | Arg | Asn | Pro | Arg | |
| | | | | 165 | | | | | 170 | | | | | 175 | | |

| ggg | gaa | gaa | ggg | gga | ccc | tgg | tgt | ttc | aca | agc | aat | cca | gag | gta | cgc | 576 |
|---|---|---|---|---|---|---|---|---|---|---|---|---|---|---|---|---|
| Gly | Glu | Glu | Gly | Gly | Pro | Trp | Cys | Phe | Thr | Ser | Asn | Pro | Glu | Val | Arg | |
| | | | 180 | | | | | 185 | | | | | 190 | | | |

| tac | gaa | gtc | tgt | gac | att | cct | cag | tgt | tca | gaa | gtt | gaa | tgc | atg | acc | 624 |
|---|---|---|---|---|---|---|---|---|---|---|---|---|---|---|---|---|
| Tyr | Glu | Val | Cys | Asp | Ile | Pro | Gln | Cys | Ser | Glu | Val | Glu | Cys | Met | Thr | |
| | | 195 | | | | | 200 | | | | | 205 | | | | |

| tgc | aat | ggg | gag | agt | tat | cga | ggt | ctc | atg | gat | cat | aca | gaa | tca | ggc | 672 |
|---|---|---|---|---|---|---|---|---|---|---|---|---|---|---|---|---|
| Cys | Asn | Gly | Glu | Ser | Tyr | Arg | Gly | Leu | Met | Asp | His | Thr | Glu | Ser | Gly | |
| | 210 | | | | | 215 | | | | | 220 | | | | | |

| aag | att | tgt | cag | cgc | tgg | gat | cat | cag | aca | cca | cac | cgg | cac | aaa | ttc | 720 |
|---|---|---|---|---|---|---|---|---|---|---|---|---|---|---|---|---|

```
Lys Ile Cys Gln Arg Trp Asp His Gln Thr Pro His Arg His Lys Phe
225                 230                 235                 240 ttg cct gaa aga tat ccc gac aag ggc ttt gat gat aat tat tgc cgc      768
Leu Pro Glu Arg Tyr Pro Asp Lys Gly Phe Asp Asp Asn Tyr Cys Arg
                245                 250                 255 aat ccc gat ggc cag ccg agg cca tgg tgc tat act ctt gac cct cac      816
Asn Pro Asp Gly Gln Pro Arg Pro Trp Cys Tyr Thr Leu Asp Pro His
            260                 265                 270 acc cgc tgg gag tac tgt gca att aaa aca tgc gct gac aat act atg      864
Thr Arg Trp Glu Tyr Cys Ala Ile Lys Thr Cys Ala Asp Asn Thr Met
        275                 280                 285 aat gac act gat gtt cct ttg gaa aca act gaa tgc atc caa ggt caa      912
Asn Asp Thr Asp Val Pro Leu Glu Thr Thr Glu Cys Ile Gln Gly Gln
290                 295                 300 gga gaa ggc tac agg ggc act gtc aat acc att tgg aat gga att cca      960
Gly Glu Gly Tyr Arg Gly Thr Val Asn Thr Ile Trp Asn Gly Ile Pro
305                 310                 315                 320 tgt cag cgt tgg gat tct cag tat cct cac gag cat gac atg act cct     1008
Cys Gln Arg Trp Asp Ser Gln Tyr Pro His Glu His Asp Met Thr Pro
                325                 330                 335 gaa aat ttc aag tgc aag gac cta cga gaa aat tac tgc cga aat cca     1056
Glu Asn Phe Lys Cys Lys Asp Leu Arg Glu Asn Tyr Cys Arg Asn Pro
                340                 345                 350 gat ggg tct gaa tca ccc tgg tgt ttt acc act gat cca aac atc cga     1104
Asp Gly Ser Glu Ser Pro Trp Cys Phe Thr Thr Asp Pro Asn Ile Arg
            355                 360                 365 gtt ggc tac tgc tcc caa att cca aac tgt gat atg tca cat gga caa     1152
Val Gly Tyr Cys Ser Gln Ile Pro Asn Cys Asp Met Ser His Gly Gln
        370                 375                 380 gat tgt tat cgt ggg aat ggc aaa aat tat atg ggc aac tta tcc caa     1200
Asp Cys Tyr Arg Gly Asn Gly Lys Asn Tyr Met Gly Asn Leu Ser Gln
385                 390                 395                 400 aca aga tct gga cta aca tgt tca atg tgg gac aag aac atg gaa gac     1248
Thr Arg Ser Gly Leu Thr Cys Ser Met Trp Asp Lys Asn Met Glu Asp
                405                 410                 415 tta cat cgt cat atc ttc tgg gaa cca gat gca agt aag ctg aat gag     1296
Leu His Arg His Ile Phe Trp Glu Pro Asp Ala Ser Lys Leu Asn Glu
                420                 425                 430 aat tac tgc cga aat cca gat gat gat gct cat gga ccc tgg tgc tac     1344
Asn Tyr Cys Arg Asn Pro Asp Asp Asp Ala His Gly Pro Trp Cys Tyr
            435                 440                 445 acg gga aat cca ctc att cct tgg gat tat tgc cct att tct cgt tgt     1392
Thr Gly Asn Pro Leu Ile Pro Trp Asp Tyr Cys Pro Ile Ser Arg Cys
        450                 455                 460 gaa ggt gat acc aca cct aca ata gtc aat tta gac cat ccc gta ata     1440
Glu Gly Asp Thr Thr Pro Thr Ile Val Asn Leu Asp His Pro Val Ile
465                 470                 475                 480 tct tgt gcc aaa acg aaa caa ttg cga gtt gta aat ggg att cca aca     1488
Ser Cys Ala Lys Thr Lys Gln Leu Arg Val Val Asn Gly Ile Pro Thr
                485                 490                 495 cga aca aac ata gga tgg atg gtt agt ttg aga tac aga aat aaa cat     1536
Arg Thr Asn Ile Gly Trp Met Val Ser Leu Arg Tyr Arg Asn Lys His
                500                 505                 510 atc tgc gga gga tca ttg ata aag gag agt tgg gtt ctt act gca cga     1584
Ile Cys Gly Gly Ser Leu Ile Lys Glu Ser Trp Val Leu Thr Ala Arg
            515                 520                 525 cag tgt ttc cct tct cga gac ttg aaa gat tat gaa gct tgg ctt gga     1632
Gln Cys Phe Pro Ser Arg Asp Leu Lys Asp Tyr Glu Ala Trp Leu Gly
        530                 535                 540
```

```
att cat gat gtc cac gga aga gga gat gag aaa tgc aaa cag gtt ctc    1680
Ile His Asp Val His Gly Arg Gly Asp Glu Lys Cys Lys Gln Val Leu
545                 550                 555                 560 aat gtt tcc cag ctg gta tat ggc cct gaa gga tca gat ctg gtt tta    1728
Asn Val Ser Gln Leu Val Tyr Gly Pro Glu Gly Ser Asp Leu Val Leu
                565                 570                 575 atg aag ctt gcc agg cct gct gtc ctg gat gat ttt gtt agt acg att    1776
Met Lys Leu Ala Arg Pro Ala Val Leu Asp Asp Phe Val Ser Thr Ile
            580                 585                 590 gat tta cct aat tat gga tgc aca att cct gaa aag acc agt tgc agt    1824
Asp Leu Pro Asn Tyr Gly Cys Thr Ile Pro Glu Lys Thr Ser Cys Ser
        595                 600                 605 gtt tat ggc tgg ggc tac act gga ttg atc aac tat gat ggc cta tta    1872
Val Tyr Gly Trp Gly Tyr Thr Gly Leu Ile Asn Tyr Asp Gly Leu Leu
    610                 615                 620 cga gtg gca cat ctc tat ata atg gga aat gag aaa tgc agc cag cat    1920
Arg Val Ala His Leu Tyr Ile Met Gly Asn Glu Lys Cys Ser Gln His
625                 630                 635                 640 cat cga ggg aag gtg act ctg aat gag tct gaa ata tgt gct ggg gct    1968
His Arg Gly Lys Val Thr Leu Asn Glu Ser Glu Ile Cys Ala Gly Ala
                645                 650                 655 gaa aag att gga tca gga cca tgt gag ggg gat tat ggt ggc cca ctt    2016
Glu Lys Ile Gly Ser Gly Pro Cys Glu Gly Asp Tyr Gly Gly Pro Leu
            660                 665                 670 gtt tgt gag caa cat aaa atg aga atg gtt ctt ggt gtc att gtt cct    2064
Val Cys Glu Gln His Lys Met Arg Met Val Leu Gly Val Ile Val Pro
        675                 680                 685 ggt cgt gga tgt gcc att cca aat cgt cct ggt att ttt gtc cga gta    2112
Gly Arg Gly Cys Ala Ile Pro Asn Arg Pro Gly Ile Phe Val Arg Val
    690                 695                 700 gca tat tat gca aaa tgg ata cac aaa att att tta aca tat aag gta    2160
Ala Tyr Tyr Ala Lys Trp Ile His Lys Ile Ile Leu Thr Tyr Lys Val
705                 710                 715                 720 cca cag tca tag                                                    2172
Pro Gln Ser <210> SEQ ID NO 10
<211> LENGTH: 723
<212> TYPE: PRT
<213> ORGANISM: Homo sapiens

<400> SEQUENCE: 10

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125
```

```
Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
    290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
    370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Ala His Gly Pro Trp Cys Tyr
        435                 440                 445

Thr Gly Asn Pro Leu Ile Pro Trp Asp Tyr Cys Pro Ile Ser Arg Cys
    450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
    530                 535                 540

Ile His Asp Val His Gly Arg Gly Asp Glu Lys Cys Lys Gln Val Leu
```

-continued

```
            545                  550                  555                  560
Asn Val Ser Gln Leu Val Tyr Gly Pro Glu Gly Ser Asp Leu Val Leu
                565                  570                  575

Met Lys Leu Ala Arg Pro Ala Val Leu Asp Asp Phe Val Ser Thr Ile
                580                  585                  590

Asp Leu Pro Asn Tyr Gly Cys Thr Ile Pro Glu Lys Thr Ser Cys Ser
                595                  600                  605

Val Tyr Gly Trp Gly Tyr Thr Gly Leu Ile Asn Tyr Asp Gly Leu Leu
                610                  615                  620

Arg Val Ala His Leu Tyr Ile Met Gly Asn Glu Lys Cys Ser Gln His
625                  630                  635                  640

His Arg Gly Lys Val Thr Leu Asn Glu Ser Glu Ile Cys Ala Gly Ala
                645                  650                  655

Glu Lys Ile Gly Ser Gly Pro Cys Glu Gly Asp Tyr Gly Gly Pro Leu
                660                  665                  670

Val Cys Glu Gln His Lys Met Arg Met Val Leu Gly Val Ile Val Pro
                675                  680                  685

Gly Arg Gly Cys Ala Ile Pro Asn Arg Pro Gly Ile Phe Val Arg Val
                690                  695                  700

Ala Tyr Tyr Ala Lys Trp Ile His Lys Ile Ile Leu Thr Tyr Lys Val
705                  710                  715                  720

Pro Gln Ser
```

<210> SEQ ID NO 11
<211> LENGTH: 2136
<212> TYPE: DNA
<213> ORGANISM: Homo sapiens

<400> SEQUENCE: 11

```
atggggtggc tcccactcct gctgcttctg actcaatgct tagggggtccc tgggcagcgc      60
tcgccattga atgacttcca agtgctccgg ggcacagagc tacagcacct gctacatgcg     120
gtggtgcccg ggccttggca ggaggatgtg gcagatgctg aagagtgtgc tggtcgctgt     180
gggcccttaa tggactgccg ggccttccac tacaacgtga gcagccatgg ttgccaactg     240
ctgccatgga ctcaacactc gccccacacg aggctgcggc gttctgggcg ctgtgacctc     300
ttccagaaga aagactacgt acggacctgc atcatgaaca atggggttgg gtaccggggc     360
accatggcca cgaccgtggg tggcctgccc tgccaggctt ggagccacaa gttcccgaat     420
gatcacaagt acacgcccac tctccggaat ggcctggaag agaacttctg ccgtaaccct     480
gatggcgacc ccgagggtcc ttggtgctac acaacagacc ctgctgtgcg cttccagagc     540
tgcggcatca atcctgccg ggaggccgcg tgtgtctggt gcaatggcga ggaataccgc     600
ggcgcggtag accgcacgga gtcagggcgc gagtgccagc gctgggatct tcagcacccg     660
caccagcacc ccttcgagcc gggcaagttc ctcgaccaag gtctggacga caactattgc     720
cggaatcctg acggctccga gcggccatgg tgctacacta cggatccgca gatcgagcga     780
gagttctgtg acctccccccg ctgcgggtcc gaggcacagc cccgccaaga ggccacaact     840
gtcagctgct ccgcgggaa gggtgagggc taccggggca cagccaatac caccactgcg     900
ggcgtacctt gccagcgttg ggacgcgcaa atcccgcatc agcaccgatt tacgccagaa     960
aaatacgcgt gcaaagacct tcgggagaac ttctgccgga accccgacgg ctcagaggcg    1020
ccctggtgct tcacactgcg gcccggcatg cgcgcggcct tttgctacca gatccggcgt    1080
tgtacagacg acgtgcggcc ccaggactgc taccacggcg caggggagca gtaccgcggc    1140
```

```
acggtcagca agacccgcaa gggtgtccag tgccagcgct ggtccgctga gacgccgcac    1200
aagccgcagt tcacgtttac ctccgaaccg catgcacaac tggaggagaa cttctgccgg    1260
aacccagatg gggatagcca tgggccctgg tgctacacga tggacccaag acccccattc    1320
gactactgtg ccctgcgacg ctgcgctgat gaccagccgc catcaatcct ggaccccca    1380 gaccaggtgc agtttgagaa gtgtggcaag agggtggatc ggctggatca gcggcgttcc    1440
aagctgcgcg tggttggggg ccatccgggc aactcaccct ggacagtcag cttgcggaat    1500
cggcagggcc agcatttctg cggggggtct ctagtgaagg agcagtggat actgactgcc    1560
cggcagtgct tctcctcctg ccatatgcct ctcacgggct atgaggtatg gttgggcacc    1620
ctgttccaga acccacagca tggagagcca agcctacagc gggtcccagt agccaagatg    1680
gtgtgtgggc cctcaggctc ccagcttgtc ctgctcaagc tggagagatc tgtgaccctg    1740
aaccagcgtg tggccctgat ctgcctgccc cctgaatggt atgtggtgcc tccagggacc    1800
aagtgtgaga ttgcaggctg gggtgagacc aaaggtacgg gtaatgacac agtcctaaat    1860 gtggccttc tgaatgttat ctccaaccag gagtgtaaca tcaagcaccg aggacgtgtg    1920
cgggagagtg agatgtgcac tgagggactg ttggcccctg tggggcctg tgagggtgac    1980 tacgggggcc cacttgcctg ctttacccac aactgctggg tcctggaagg aattataatc    2040
cccaaccgag tatgcgcaag gtcccgctgg ccagctgtct tcacgcgtgt ctctgtgttt    2100
gtggactgga ttcacaaggt catgagactg ggttag                              2136
```

<210> SEQ ID NO 12
<211> LENGTH: 711
<212> TYPE: PRT
<213> ORGANISM: Homo sapiens

<400> SEQUENCE: 12

```
Met Gly Trp Leu Pro Leu Leu Leu Leu Thr Gln Cys Leu Gly Val
1               5                   10                  15

Pro Gly Gln Arg Ser Pro Leu Asn Asp Phe Gln Val Leu Arg Gly Thr
            20                  25                  30

Glu Leu Gln His Leu Leu His Ala Val Val Pro Gly Pro Trp Gln Glu
        35                  40                  45

Asp Val Ala Asp Ala Glu Glu Cys Ala Gly Arg Cys Gly Pro Leu Met
    50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
        115                 120                 125

Leu Pro Cys Gln Ala Trp Ser His Lys Phe Pro Asn Asp His Lys Tyr
    130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
            180                 185                 190
```

-continued

```
Trp Cys Asn Gly Glu Glu Tyr Arg Gly Ala Val Asp Arg Thr Glu Ser
            195                 200                 205

Gly Arg Glu Cys Gln Arg Trp Asp Leu Gln His Pro His Gln His Pro
    210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
    275                 280                 285

Glu Gly Tyr Arg Gly Thr Ala Asn Thr Thr Thr Ala Gly Val Pro Cys
290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
            340                 345                 350

Ala Phe Cys Tyr Gln Ile Arg Arg Cys Thr Asp Asp Val Arg Pro Gln
    355                 360                 365

Asp Cys Tyr His Gly Ala Gly Glu Gln Tyr Arg Gly Thr Val Ser Lys
370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
    435                 440                 445

Ala Asp Asp Gln Pro Pro Ser Ile Leu Asp Pro Pro Asp Gln Val Gln
450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
            500                 505                 510

Lys Glu Gln Trp Ile Leu Thr Ala Arg Gln Cys Phe Ser Ser Cys His
    515                 520                 525

Met Pro Leu Thr Gly Tyr Glu Val Trp Leu Gly Thr Leu Phe Gln Asn
530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
                565                 570                 575

Ser Val Thr Leu Asn Gln Arg Val Ala Leu Ile Cys Leu Pro Pro Glu
            580                 585                 590

Trp Tyr Val Val Pro Pro Gly Thr Lys Cys Glu Ile Ala Gly Trp Gly
    595                 600                 605

Glu Thr Lys Gly Thr Gly Asn Asp Thr Val Leu Asn Val Ala Phe Leu
```

```
             610                 615                 620
Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
                645                 650                 655

Cys Glu Gly Asp Tyr Gly Gly Pro Leu Ala Cys Phe Thr His Asn Cys
                660                 665                 670

Trp Val Leu Glu Gly Ile Ile Ile Pro Asn Arg Val Cys Ala Arg Ser
                675                 680                 685

Arg Trp Pro Ala Val Phe Thr Arg Val Ser Val Phe Val Asp Trp Ile
            690                 695                 700

His Lys Val Met Arg Leu Gly
705                 710

<210> SEQ ID NO 13
<211> LENGTH: 12
<212> TYPE: PRT
<213> ORGANISM: Artificial Sequence
<220> FEATURE:
<223> OTHER INFORMATION: Derived from Homo sapiens

<400> SEQUENCE: 13

Gly Asn Ser Ala Val Asp His His His His His His
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Derived from Homo sapiens

<400> SEQUENCE: 14

Leu Arg Val Val
1

<210> SEQ ID NO 15
<211> LENGTH: 8
<212> TYPE: PRT
<213> ORGANISM: Artificial Sequence
<220> FEATURE:
<223> OTHER INFORMATION: Derived from Homo sapiens

<400> SEQUENCE: 15

Arg Thr Lys Arg Leu Arg Val Val
1               5

<210> SEQ ID NO 16
<211> LENGTH: 36
<212> TYPE: DNA
<213> ORGANISM: Artificial Sequence
<220> FEATURE:
<223> OTHER INFORMATION: Primer derived from Homo sapiens

<400> SEQUENCE: 16
ccaccgcggt ggcggccgct ctagaactag tggatc                            36

<210> SEQ ID NO 17
<211> LENGTH: 30
<212> TYPE: DNA
<213> ORGANISM: Artificial Sequence
<220> FEATURE:
<223> OTHER INFORMATION: Primer derived from Homo sapiens
```

```
<400> SEQUENCE: 17
gcccccaacc actcgcaatt gtttcgtttt                              30

<210> SEQ ID NO 18
<211> LENGTH: 12
<212> TYPE: DNA
<213> ORGANISM: Artificial Sequence
<220> FEATURE:
<223> OTHER INFORMATION: Derived from Homo sapiens

<400> SEQUENCE: 18
ttgcgagtgg tt                                                 12

<210> SEQ ID NO 19
<211> LENGTH: 30
<212> TYPE: DNA
<213> ORGANISM: Artificial Sequence
<220> FEATURE:
<223> OTHER INFORMATION: Primer derived from Homo sapiens

<400> SEQUENCE: 19
aaacaattgc gagtggttgg gggccatccg                              30

<210> SEQ ID NO 20
<211> LENGTH: 69
<212> TYPE: DNA
<213> ORGANISM: Artificial Sequence
<220> FEATURE:
<223> OTHER INFORMATION: Primer derived from Homo sapiens

<400> SEQUENCE: 20
cccaagcttt caatgatgat gatgatgatg atggtcgacg gcgctatccc acccagtctc    60
atgaccttg                                                     69

<210> SEQ ID NO 21
<211> LENGTH: 4
<212> TYPE: PRT
<213> ORGANISM: Artificial Sequence
<220> FEATURE:
<223> OTHER INFORMATION: Derived from Homo sapiens

<400> SEQUENCE: 21

Arg Thr Lys Arg
 1

<210> SEQ ID NO 22
<211> LENGTH: 30
<212> TYPE: DNA
<213> ORGANISM: Artificial Sequence
<220> FEATURE:
<223> OTHER INFORMATION: Primer derived from Homo sapiens

<400> SEQUENCE: 22
atcccaaaca agatctggac taacatgttc                              30

<210> SEQ ID NO 23
<211> LENGTH: 34
<212> TYPE: DNA
<213> ORGANISM: Artificial Sequence
<220> FEATURE:
<223> OTHER INFORMATION: Primer derived from Homo sapiens

<400> SEQUENCE: 23
ctcgcaatcg tttcgttctg gcacaagata ttac                         34
```

<210> SEQ ID NO 24
<211> LENGTH: 31
<212> TYPE: DNA
<213> ORGANISM: Artificial Sequence
<220> FEATURE:
<223> OTHER INFORMATION: Primer derived from Homo sapiens

<400> SEQUENCE: 24
tcttgtgcca gaacgaaacg attgcgagtg g                          31

<210> SEQ ID NO 25
<211> LENGTH: 24
<212> TYPE: DNA
<213> ORGANISM: Artificial Sequence
<220> FEATURE:
<223> OTHER INFORMATION: Primer derived from Homo sapiens

<400> SEQUENCE: 25
ggtcacagat ctctccagct tgag                                  24

<210> SEQ ID NO 26
<211> LENGTH: 5
<212> TYPE: PRT
<213> ORGANISM: Artificial Sequence
<220> FEATURE:
<223> OTHER INFORMATION: Derived from Homo sapiens

<400> SEQUENCE: 26

Leu Leu Arg Val Val
1               5

<210> SEQ ID NO 27
<211> LENGTH: 487
<212> TYPE: PRT
<213> ORGANISM: Homo sapiens

<400> SEQUENCE: 27

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg

```
                   180                 185                 190
Tyr Glu Val Cys Asp Ile Pro Gln Cys Ser Glu Val Glu Cys Met Thr
            195                 200                 205

Cys Asn Gly Glu Ser Tyr Arg Gly Leu Met Asp His Thr Glu Ser Gly
        210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
        370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Asp Ala His Gly Pro Trp Cys Tyr
        435                 440                 445

Thr Gly Asn Pro Leu Ile Pro Trp Asp Tyr Cys Pro Ile Ser Arg Cys
        450                 455                 460

Glu Gly Asp Thr Thr Pro Thr Ile Val Asn Leu Asp His Pro Val Ile
465                 470                 475                 480

Ser Cys Ala Lys Thr Lys Gln
                485

<210> SEQ ID NO 28
<211> LENGTH: 226
<212> TYPE: PRT
<213> ORGANISM: Homo sapiens

<400> SEQUENCE: 28

Gly Gly His Pro Gly Asn Ser Pro Trp Thr Val Ser Leu Arg Asn Arg
1               5                   10                  15

Gln Gly Gln His Phe Cys Gly Gly Ser Leu Val Lys Glu Gln Trp Ile
            20                  25                  30

Leu Thr Ala Arg Gln Cys Phe Ser Ser Cys His Met Pro Leu Thr Gly
        35                  40                  45

Tyr Glu Val Trp Leu Gly Thr Leu Phe Gln Asn Pro Gln His Gly Glu
    50                  55                  60
```

-continued

```
Pro Ser Leu Gln Arg Val Pro Val Ala Lys Met Val Cys Gly Pro Ser
 65                  70                  75                  80

Gly Ser Gln Leu Val Leu Leu Lys Leu Glu Arg Ser Val Thr Leu Asn
                 85                  90                  95

Gln Arg Val Ala Leu Ile Cys Leu Pro Pro Glu Trp Tyr Val Val Pro
                100                 105                 110

Pro Gly Thr Lys Cys Glu Ile Ala Gly Trp Gly Glu Thr Lys Gly Thr
            115                 120                 125

Gly Asn Asp Thr Val Leu Asn Val Ala Phe Leu Asn Val Ile Ser Asn
        130                 135                 140

Gln Glu Cys Asn Ile Lys His Arg Gly Arg Val Arg Glu Ser Glu Met
145                 150                 155                 160

Cys Thr Glu Gly Leu Leu Ala Pro Val Gly Ala Cys Glu Gly Asp Tyr
                165                 170                 175

Gly Gly Pro Leu Ala Cys Phe Thr His Asn Cys Trp Val Leu Glu Gly
            180                 185                 190

Ile Ile Ile Pro Asn Arg Val Cys Ala Arg Ser Arg Trp Pro Ala Val
        195                 200                 205

Phe Thr Arg Val Ser Val Phe Val Asp Trp Ile His Lys Val Met Arg
    210                 215                 220

Leu Gly
225
```